US009383342B1

(12) United States Patent
Bossi et al.

(10) Patent No.: US 9,383,342 B1
(45) Date of Patent: *Jul. 5, 2016

(54) ULTRASOUND INSPECTION SYSTEM FOR INSPECTING A TEST OBJECT WITH NON-PLANAR FEATURES

(75) Inventors: Richard H. Bossi, Renton, WA (US); Gary E. Georgeson, Tacoma, WA (US); Clarence L. Gordon, III, Renton, WA (US); Jeffrey R. Kollgaard, Seattle, WA (US); William P. Motzer, Seattle, WA (US); Alan Frank Stewart, Renton, WA (US)

(73) Assignee: THE BOEING COMPANY, Chicago, IL (US)

( * ) Notice: Subject to any disclaimer, the term of this patent is extended or adjusted under 35 U.S.C. 154(b) by 219 days.

This patent is subject to a terminal disclaimer.

(21) Appl. No.: 13/526,853

(22) Filed: Jun. 19, 2012

(51) Int. Cl.
*G01N 29/24* (2006.01)
*G01N 29/265* (2006.01)
*G01N 21/17* (2006.01)

(52) U.S. Cl.
CPC ........ *G01N 29/2418* (2013.01); *G01N 21/1702* (2013.01); *G01N 2291/0231* (2013.01); *G01N 2291/2694* (2013.01)

(58) Field of Classification Search
CPC .............. G01N 29/2418; G01N 29/11; G01N 2291/0231; G01N 21/17; G01N 21/84; G01N 29/14; G01N 29/24; G01N 29/04; G01N 29/265; G01N 2291/2694; G01N 21/1702; G01H 9/00; G06F 19/321; G02B 6/02
USPC ............ 73/643, 655, 584, 621, 657, 865, 8.1, 73/1.79, 634, 620, 596, 627, 653; 382/128; 356/73.1, 28.5, 502, 72
See application file for complete search history.

(56) References Cited

U.S. PATENT DOCUMENTS

| 4,295,738 A | 10/1981 | Meltz et al. |
| 4,567,769 A * | 2/1986 | Barkhoudarian ............... 73/643 |
| 5,760,904 A | 6/1998 | Lorraine et al. |
| 6,144,685 A | 11/2000 | Iwasa et al. |
| 6,901,157 B2 * | 5/2005 | Ogawa .......................... 382/128 |
| 7,042,563 B2 | 5/2006 | Wilsher et al. |
| 7,369,250 B2 * | 5/2008 | Dubois et al. ................. 356/502 |
| 7,576,848 B2 | 8/2009 | Dubois et al. |
| 7,784,348 B2 * | 8/2010 | Dubois et al. ................... 73/621 |
| 7,791,739 B2 | 9/2010 | Dubois et al. |

(Continued)

OTHER PUBLICATIONS

Fomitchov et al., "Laser Ultrasonic Array System for Real-Time Cure Monitoring of Polymer-Matrix Composites," Journal of Composite Materials, vol. 36, No. 15, Aug. 2002, pp. 1889-1901.

(Continued)

*Primary Examiner* — Laura Martin
*Assistant Examiner* — Rose M Miller
(74) *Attorney, Agent, or Firm* — Yee & Associates, P.C.

(57) ABSTRACT

A method and apparatus for inspecting a test object with a non-planar feature. A pattern of light is transmitted from a first array of optical fibers associated with a sensor structure onto a surface of the test object at a location of the non-planar feature. The pattern of light is configured to cause sound waves in the test object when the pattern of light encounters the test object. A response to the sound waves is detected using a second array of optical fibers associated with the sensor structure. A determination is made as to whether an inconsistency is present in the test object at the location of the non-planar feature from the response to the sound waves detected using the second array of optical fibers.

18 Claims, 16 Drawing Sheets

(56) References Cited

U.S. PATENT DOCUMENTS

| | | | |
|---|---|---|---|
| 7,800,762 B2 | 9/2010 | Deaton, Jr. et al. | |
| 7,865,316 B2 | 1/2011 | Turner et al. | |
| 8,109,160 B2 | 2/2012 | Bossi et al. | |
| 8,224,485 B2 | 7/2012 | Unsworth | |
| 8,312,773 B2 * | 11/2012 | Fomitchov | 73/643 |
| 2004/0003662 A1 | 1/2004 | Kenderian et al. | |
| 2008/0291963 A1 | 11/2008 | Deaton, Jr. et al. | |
| 2010/0139405 A1 * | 6/2010 | Melikechi et al. | 73/655 |
| 2010/0154549 A1 * | 6/2010 | Fomitchov | 73/643 |
| 2010/0291599 A1 | 11/2010 | Tague, Jr. et al. | |
| 2012/0304774 A1 | 12/2012 | Ishioka | |

OTHER PUBLICATIONS

Wang et al., "Beam shaping technology for laser diode arrays," Proceedings of SPIE, vol. 4770, Jul. 2002, pp. 131-135.

Georgeson et al., "Ultrasound Inspection System of Limited Access Composite Structures," U.S. Appl. No. 13/526,698, filed Jun. 19, 2012, (74 Pages).

Bossi et al., "Laser Ultrasound Array System," U.S. Appl. No. 13/527,021, filed Jun. 19, 2012, (63 Pages).

Bossi et al., "Ultrasound Inspection System for Inspecting a Test Object with Non-Planar Features," U.S. Appl. No. 13/596,977, filed Aug. 28, 2012, 107 pages.

Intellectual Property Office of Singapore Search Report and Written Opinion, dated Jul. 3, 2014, regarding Application No. 201304652-9, 12 pages.

Office Action, dated May 8, 2014, regarding U.S. Appl. No. 13/526,698, 31 pages.

Office Action, dated Jun. 25, 2014, regarding U.S. Appl. No. 13/527,021, 28 pages.

Office Action, dated Jan. 30, 2015, regarding U.S. Appl. No. 13/526,698, 32 pages.

Office Action, dated Jan. 5, 2015, regarding U.S. Appl. No. 13/527,021, 25 pages.

Office Action, dated Feb. 18, 2015, regarding U.S. Appl. No. 13/596,944, 31 pages.

Office Action, dated Apr. 14, 2015, regarding U.S. Appl. No. 13/526,698, 17 pages.

Office Action, dated Apr. 15, 2015, regarding U.S. Appl. No. 13/527,021, 17 pages.

Notice of Allowance, dated Jun. 5, 2015, regarding U.S. Appl. No. 13/527,021, 11 pages.

Notice of Allowance, dated Jul. 7, 2015, regarding U.S. Appl. No. 13/526,698, 9 pages.

Notice of Allowance, dated Sep. 4, 2015, regarding U.S. Appl. No. 14/149,887, 21 pages.

Final Office Action, dated Oct. 6, 2014, regarding U.S. Appl. No. 13/526,698, 33 pages.

Final Office Action, dated Oct. 28, 2014, regarding U.S. Appl. No. 13/527,021, 33 pages.

* cited by examiner

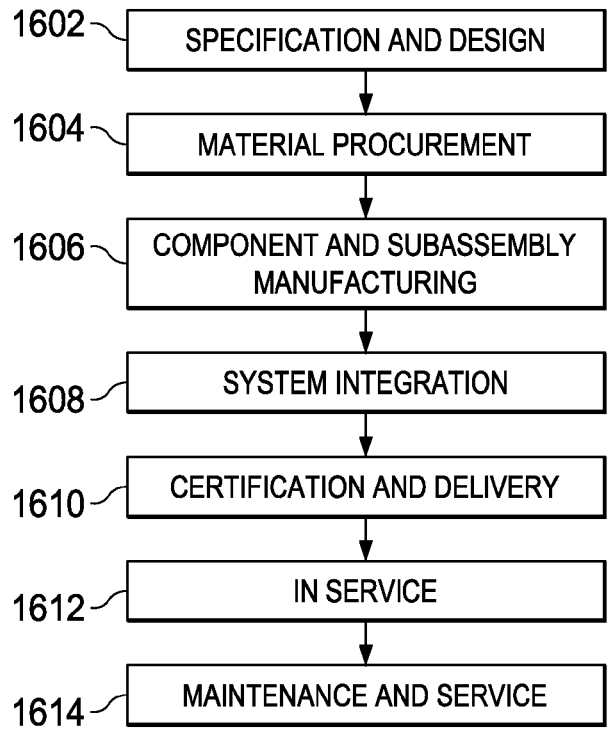
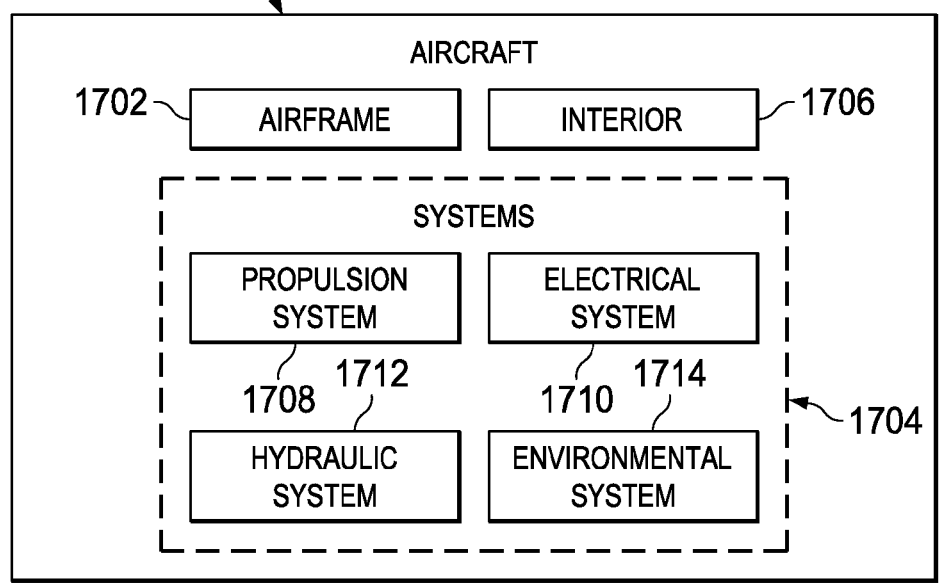

ULTRASOUND INSPECTION SYSTEM FOR INSPECTING A TEST OBJECT WITH NON-PLANAR FEATURES

CROSS-REFERENCE TO RELATED APPLICATION

This application is related to the following patent application: entitled "Laser Ultrasound Array System," Ser. No. 13/527,021; filed of even date herewith, assigned to the same assignee, and incorporated herein by reference. This application is also related to the following patent application: entitled "Ultrasound Inspection System of Limited Access Composite Structures," Ser. No. 13/526,698; filed Jun. 19, 2012.

BACKGROUND INFORMATION

1. Field

The present disclosure relates generally to inspecting objects and, in particular, to performing nondestructive inspection of objects. Still more particularly, the present disclosure relates to a method and apparatus for inspecting objects using ultrasound.

2. Background

In manufacturing aircraft, vehicles, and other structures, inspection of parts used to form these structures is often performed to determine whether the parts will have desired parameters for a desired performance of the part. Nondestructive testing is commonly performed on these parts. Nondestructive testing is used to evaluate properties of a part without altering the ability of the part to be employed in service. Nondestructive testing may include ultrasound testing, eddy current testing, x-ray testing, visual inspections, and other types of testing.

Ultrasound testing is often used to perform inspections on aircraft parts that include or are comprised of composite materials. Ultrasound testing involves transmitting sound waves through a test object. A response to these sound waves is detected. The response is analyzed to determine whether inconsistencies are present in the test object.

Ultrasound testing is commonly performed using a transducer. The transducer is configured to send sound waves into a test object and detect a response to the sound waves. The transducer is typically coupled to a surface of the test object. This coupling involves physical contact between the transducer and the test object.

In many cases, a coupling medium is also employed. For example, water, oil, a water-based gel, or some other liquid may be used. This coupling medium is used to reduce the acoustic impedance between the transducer and the test object.

In some cases, coupling the transducer to the surface of the test object may be more difficult to perform than desired. Difficulty in coupling a transducer to the surface of the test object may occur when the test object has a non-planar surface. In other words, the surface of the test object may have non-planar features. The non-planar feature may be a radius, an edge, a curve, an angle, or other types of non-planar features. When non-planar features are present on the surface of a test object, more difficulty may occur than desired when attempting to ensure that sound enters the test object in a direction that is substantially perpendicular to the surface of the test object. For layered materials such as carbon fiber laminates, perpendicular sound entry is particularly desirable during the inspection process.

Further, the use of a coupling medium may be undesirable with some test objects. For example, the use of a coupling medium may take more time and effort than desired or may be detrimental to the test object.

Therefore, it would be desirable to have a method and apparatus that takes into account at least some of the issues discussed above, as well as possibly other issues.

SUMMARY

In one illustrative embodiment, a method is present for inspecting a test object with a non-planar feature. A pattern of light is transmitted from a first array of optical fibers associated with a sensor structure onto a surface of the test object at a location of the non-planar feature. The pattern of light is configured to cause sound waves in the test object when the pattern of light encounters the test object. A response to the sound waves is detected using a second array of optical fibers associated with the sensor structure. A determination is made as to whether an inconsistency is present in the test object at the location of the non-planar feature from the response to the sound waves detected using the second array of optical fibers.

In another illustrative embodiment, a method is present for inspecting a test object with a non-planar feature. A portion of the test object with the non-planar feature is identified for inspection. A sensor is moved to a location in the portion of the test object. A pattern of light is transmitted from a first array of optical fibers associated with a sensor structure onto a surface of the test object at a location of the non-planar feature. The pattern of light is configured to cause sound waves in the test object when the pattern of light encounters the surface of the test object. A response to the sound waves is detected using a second array of optical fibers associated with the sensor structure. A determination is made as to whether an inconsistency is present in the test object at the location of the non-planar feature from the response to the sound waves detected using the second array of optical fibers associated with the sensor structure. Another location is identified as the location. The steps of moving, transmitting, detecting, and determining are repeated until all of the portion of the test object has been scanned.

In yet another illustrative embodiment, an apparatus for inspecting a test object with a non-planar feature comprises a sensor structure, a first array of optical fibers, and a second array of optical fibers. The first array of optical fibers is associated with the sensor structure and is configured to transmit a pattern of light towards the test object having the non-planar feature. The pattern of light is configured to cause sound waves in the test object when the pattern of light encounters the test object. The second array of optical fibers is associated with the sensor structure and is configured to detect a response to the sound waves.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

FIG. 16 is an illustration of an aircraft manufacturing and service method in accordance with an illustrative embodiment; and FIG. 17 is an illustration of an aircraft in which an illustrative embodiment may be implemented.

DETAILED DESCRIPTION

The illustrative embodiments recognize and take into account one or more different considerations. For example, the illustrative embodiments recognize and take into account that one solution may involve using light, such as coherent light, to generate sound waves and detect responses to the sound waves in a test object.

The illustrative embodiments recognize and take into account that a laser ultrasound inspection system may be used to perform inspections of a test object, such as an aircraft part, and in particular, a composite aircraft part. With a laser ultrasound inspection system, physical contact between the sensor and the test object is unnecessary.

The illustrative embodiments recognize and take into account that currently available laser ultrasound inspection systems employ a laser beam that may be scanned across the surface of the test object. The scanning of the laser beam may be performed in a manner such that sound waves travel in a direction into the test object that is substantially perpendicular to the surface of the test object.

The illustrative embodiments recognize and take into account, however, that with currently available laser ultrasound inspection systems, these systems may be more difficult to use than desired. Also, these currently available laser ultrasound inspection systems are often slower than transducer based ultrasound inspection systems when inspecting test objects.

For example, the illustrative embodiments recognize and take into account that scanning a beam across a surface of a test object may take more time than desired. For example, the amount of time needed to scan a test object, such as a wing, may take more time than desired when manufacturing an aircraft.

The illustrative embodiments also recognize and take into account that this type of laser ultrasound inspection system may require placement of the part in a eye-safe room that is configured to avoid undesired exposure by human operators to the laser beam generated by the laser ultrasound inspection system. The illustrative embodiments recognize and take into account that currently available laser ultrasound inspection systems may be more expensive and more complex than desired.

Figure 1:
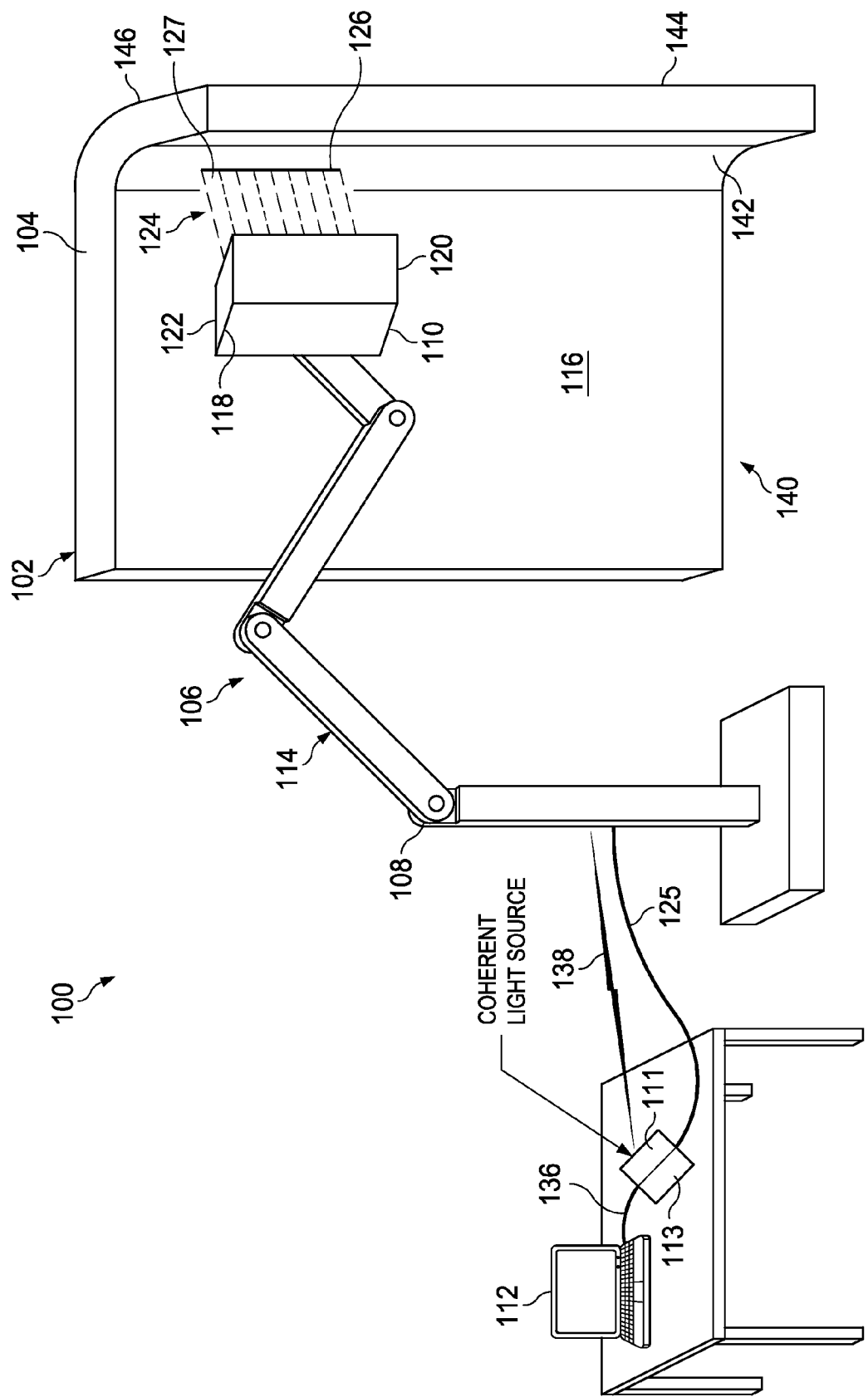
FIG. 1 is an illustration of an inspection environment in accordance with an illustrative embodiment.

With reference now to the figures, and in particular, with reference to FIG. 1, an illustration of an inspection environment is depicted in accordance with an illustrative embodiment. As depicted, inspection environment 100 includes test object 102. In this illustrative example, test object 102 takes the form of composite test object 104. Laser ultrasound inspection system 106 may be used to inspect test object 102.

As depicted, laser ultrasound inspection system 106 comprises robot 108, end effector 110, coherent light source 111, computer 112, and interferometer system 113. Robot 108 takes the form of scanning robot arm 114 in this illustrative example. Robot 108 is configured to move end effector 110 relative to surface 116 of test object 102.

In this illustrative example, end effector 110 may be removably connected to robot 108. As depicted, end effector 110 takes the form of, or includes, sensor 118. Sensor 118 has laser ultrasound source 120 and laser ultrasound detector 122.

Laser ultrasound source 120 is configured to emit coherent light 124 in the form of pattern 126 onto surface 116 of test object 102. In this illustrative example, pattern 126 takes the form of line 127. Coherent light 124 has an energy that is configured to cause sound waves to travel through test object 102.

Coherent light 124 may be transmitted over communications link 125 from coherent light source 111. In this illustrative example, communications link 125 may include optical fibers. Laser ultrasound detector 122 is configured to detect a response to the sound waves generated by coherent light 124 that is emitted onto surface 116 of test object 102 in the form of pattern 126.

Laser ultrasound detector 122 transmits coherent light 124 onto surface 116 in a manner that does not cause sound waves in test object 102 and detects the response to coherent light 124. This response includes information that may be used to identify the response to the sound waves in test object 102. The light in this response is returned to interferometer system 113 over one or more optical fibers in communications link 125.

Computer 112 is configured to control operation of robot 108, coherent light source 111, and other components in laser ultrasound inspection system 106. Computer 112 is connected to coherent light source 111 and interferometer system 113 through communications link 136. Computer 112 may control the operation of coherent light source 111 and may receive data from interferometer system 113 over communications link 136. Computer 112 may communicate with robot 108 using wireless communications link 138.

Further, computer 112 is also configured to analyze the data generated by interferometer system 113 from the light detected by optical fibers in laser ultrasound detector 122. This analysis may include an indication of whether an inconsistency is present in test object 102. Computer 112 may generate a report, an image, and other suitable output based on the inspection of test object 102.

As depicted in FIG. 1, pattern 126 of coherent light 124 is moved across surface 116 of test object 102 to scan test object 102. The scanning using pattern 126 rather than a point from a beam may allow for quicker inspection of test object 102.

In this illustrative example, laser ultrasound inspection system 106 may be especially useful for inspecting non-planar features on surface 116 of test object 102. For example, end effector 110 may be moved over portions of test object 102 in which surface 116 has non-planar features 140.

For example, end effector 110 may be moved over non-planar features 140, such as radius 142 and edge 144. As another example, end effector 110 also may be used to inspect surface 146 of test object 102. This type of inspection may be more easily performed since contact between sensor 118 in end effector 110 is unnecessary when using laser ultrasound source 120 and laser ultrasound detector 122 in sensor 118.

Figure 2:
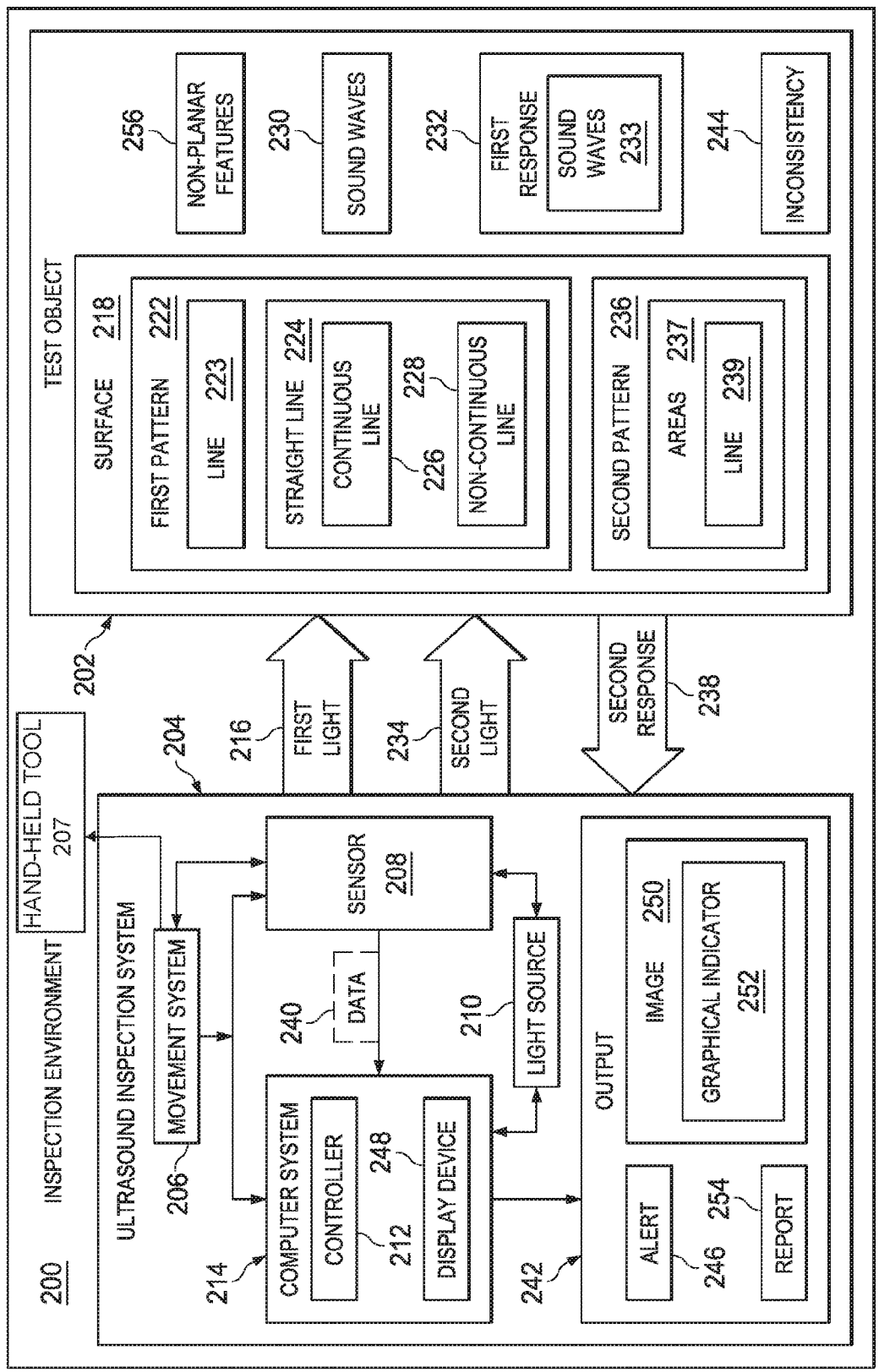
FIG. 2 is an illustration of a block diagram of an inspection environment in accordance with an illustrative embodiment.

Turning now to FIG. 2, an illustration of a block diagram of an inspection environment is depicted in accordance with an illustrative embodiment. Inspection environment 100 is one example of a physical implementation of inspection environment 200 shown in block form in this depicted example.

As depicted, inspection environment 200 includes test object 202. Test object 202 may take any number of forms. For example, test object 202 may be a part for an aircraft. Test object 202 may be comprised of different types of materials. For example, test object 202 may be comprised of a number of materials selected from at least one of a composite material, a plastic, a metal, and other suitable types of materials.

As used herein, the phrase "at least one of", when used with a list of items, means different combinations of one or more of the listed items may be used and only one of each item in the list may be needed. For example, "at least one of item A, item B, and item C" may include, without limitation, item A or item A and item B. This example also may include item A, item B, and item C, or item B and item C. In other examples, "at least one of" may be, for example, without limitation, two of item A, one of item B, and ten of item C; four of item B and seven of item C; and other suitable combinations.

In these illustrative examples, test object 202 may be a composite part for an aircraft selected from one of a panel, a fuselage barrel, a stringer, a spar, a rib, a wing box, a wing, a stabilizer, and other suitable types of parts. Test object 202 may be inspected using ultrasound inspection system 204. As depicted, ultrasound inspection system 204 includes movement system 206, sensor 208, light source 210, and controller 212.

In these illustrative examples, controller 212 controls the operation of ultrasound inspection system 204. Controller 212 may be implemented using hardware, software, or a combination of the two.

In these illustrative examples, controller 212 may be implemented within computer system 214. Computer system 214 may be one or more computers. When more than one computer is present in computer system 214, those computers may be in communication with each other through a communications medium such as a network.

When software is used, the operations performed by the components may be implemented in the program code configured to be run on a processor unit. When hardware is employed, the hardware may include circuits that operate to perform the operations in the components.

In these illustrative examples, the hardware may take the form of a circuit system, an integrated circuit, an application specific integrated circuit (ASIC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, a programmable array logic, a field programmable logic array, a field programmable gate array, and other suitable hardware devices. Additionally, the processes may be implemented in organic components integrated with inorganic components and/or may be comprised entirely of organic components excluding a human being. For example, the processes may be implemented as circuits in organic semiconductors.

Movement system 206 is configured to move sensor 208 relative to test object 202. Movement system 206 may be implemented using a number of different types of systems. For example, movement system 206 may be a robot. The robot may be, for example, a robotic arm that may move sensor 208 about a number of axes. Movement system 206 also may be, for example, without limitation, a gantry robot, a hand-operated scanning head, hand-held tool 207, and other suitable types of movement systems.

Sensor 208 is configured to transmit first light 216 onto surface 218 of test object 202. In this illustrative example, first light 216 is transmitted in a manner that forms first pattern 222 on surface 218 of test object 202. In these illustrative examples, first pattern 222 of first light 216 is a plurality of areas on which first light 216 illuminates on surface 218. These areas may be circular, oval, square, oblique, or have some other shape depending on the angle of projection onto the surface. As depicted, first pattern 222 may take the form of line 223.

First pattern 222 is straight line 224 in these illustrative examples. In other words, sensor 208 is configured to transmit first pattern 222 of first light 216 in the form of straight line 224 onto surface 218 of test object 202. In these illustrative examples, first pattern 222 may take the form of continuous line 226 or non-continuous line 228. For example, non-continuous line 228 may be a series of areas. In some illustrative examples, first pattern 222 may have a shape resembling a rectangle or other suitable shape.

First light 216 is configured to generate sound waves 230 within test object 202 when first light 216 encounters test object 202. Sound waves 230 may occur when first light 216 is transmitted onto surface 218 of test object 202. For example, energy in first light 216 may cause thermoelastic expansion in test object 202. The thermoelastic expansion may result in sound waves 230 in test object 202.

In these illustrative examples, sound waves 230 may be ultrasound sound waves. Sound waves 230 may, for example, have a frequency from about 20 kilohertz to about 10 megahertz depending on the particular implementation. The frequency for sound waves 230 may depend on the material used to form test object 202, the pulse width of the laser excitation, and other suitable factors.

Additionally, sensor 208 is configured to detect first response 232 to sound waves 230. First response 232 includes sound waves 233 that may occur as a result of scattering, reflection, modulation, and other changes to sound waves 230 traveling within test object 202. First response 232 is comprised of sound waves 233 that occur in response to sound waves 230. In this illustrative example, first response 232 is detected by sensor 208 transmitting second light 234 onto surface 218 of test object 202 and detecting second response 238 to second light 234.

In one illustrative example, second light 234 also may be transmitted in the form of second pattern 236 onto surface 218 of test object 202. In this illustrative example, second pattern 236 may take the form of areas 237 arranged in line 239. This second pattern, second pattern 236 may substantially line up with the first pattern, first pattern 222, in these illustrative examples.

Second response 238 is second light 234 that has been deflected by first response 232 in this illustrative example. First response 232, caused by sound waves 230 traveling within test object 202, may reach surface 218 and may be detected. The detection of first response 232 may be detected using an interferometer that sends a reference light, such as second light 234 and detects the mechanical vibrations on surface 218 in second response 238.

Sensor 208 sends data 240 to controller 212 when second response 238 is detected. Data 240 is used by controller 212 to generate output 242.

As depicted, output 242 may indicate whether inconsistency 244 is present in test object 202. Inconsistency 244 may be, for example, without limitation, an undesired level of porosity, delamination, and other undesired features or properties in test object 202.

Output 242 may take a number of different forms. For example, output 242 may take the form of alert 246. Alert 246 may indicate whether inconsistency 244 is present. Alert 246 may be displayed on display device 248 within computer system 214.

In another illustrative example, output 242 may be image 250. Image 250 also may be displayed on display device 248. Image 250 may be an image of a portion or all of test object 202 with graphical indicator 252 when inconsistency 244 is present in test object 202. Graphical indicator 252 may be displayed in a location in image 250 corresponding to a location in test object 202 where inconsistency 244 is detected. In other illustrative examples, if inconsistency 244 is absent, graphical indicator 252 may be displayed to indicate an absence of inconsistency 244.

As another illustrative example, output 242 may take the form of report 254. Report 254 may identify any inconsistencies in test object 202. Report 254 also may include other information, such as locations of inconsistencies, types of inconsistencies, sizes of inconsistencies, and other suitable types of information. Thus, output 242 may be at least one of alert 246, image 250 with graphical indicator 252, report 254, and other suitable types of output.

In this illustrative example, ultrasound inspection system 204 may be used to inspect portions of test object 202 in which non-planar features 256 may be present. Non-planar features 256 may be present on surface 218 of test object 202. Non-planar features 256 may include, for example, without limitation, at least one of a radius, an edge, a groove, and other non-planar features. In these illustrative examples, the edge may be an edge on a side of test object 202, an edge at a hole formed in test object 202, or some other suitable location for an edge.

Further, with ultrasound inspection system 204, sensor 208 may be positioned more closely to surface 218 of test object 202 as compared to currently used laser ultrasound inspection systems. For example, sensor 208 may be positioned from about 2 millimeters to about 10 millimeters away from surface 218 of test object 202. Of course, other distances may be used when positioning sensor 208 depending on the particular implementation.

The positioning of sensor 208 may be located such that issues with eye safety may be reduced. For example, a flexible structure such as a rubber seal or boot may be used with sensor 208 to increase eye safety without using an eye-safe room. Further, with this positioning of sensor 208, the amount of power in first light 216 and second light 234 generated by light source 210 may be reduced. As a result, a need for an eye-safe room for performing inspections of test object 202 may be avoided in some implementations.

Further, with the transmission of first light 216 as first pattern 222 and second light 234 as areas 237 in second pattern 236, the inspection of test object 202 may be performed more quickly by ultrasound inspection system 204 as compared to currently available laser ultrasound inspection systems that use a point of light. Scanning may be reduced because of the length of first pattern 222 and second pattern 236. Instead of scanning point by point, sections may be scanned by moving first pattern 222 of first light 216 and second pattern 236 of second light 234 across surface 218 of test object 202 using ultrasound inspection system 204.

Figure 3:
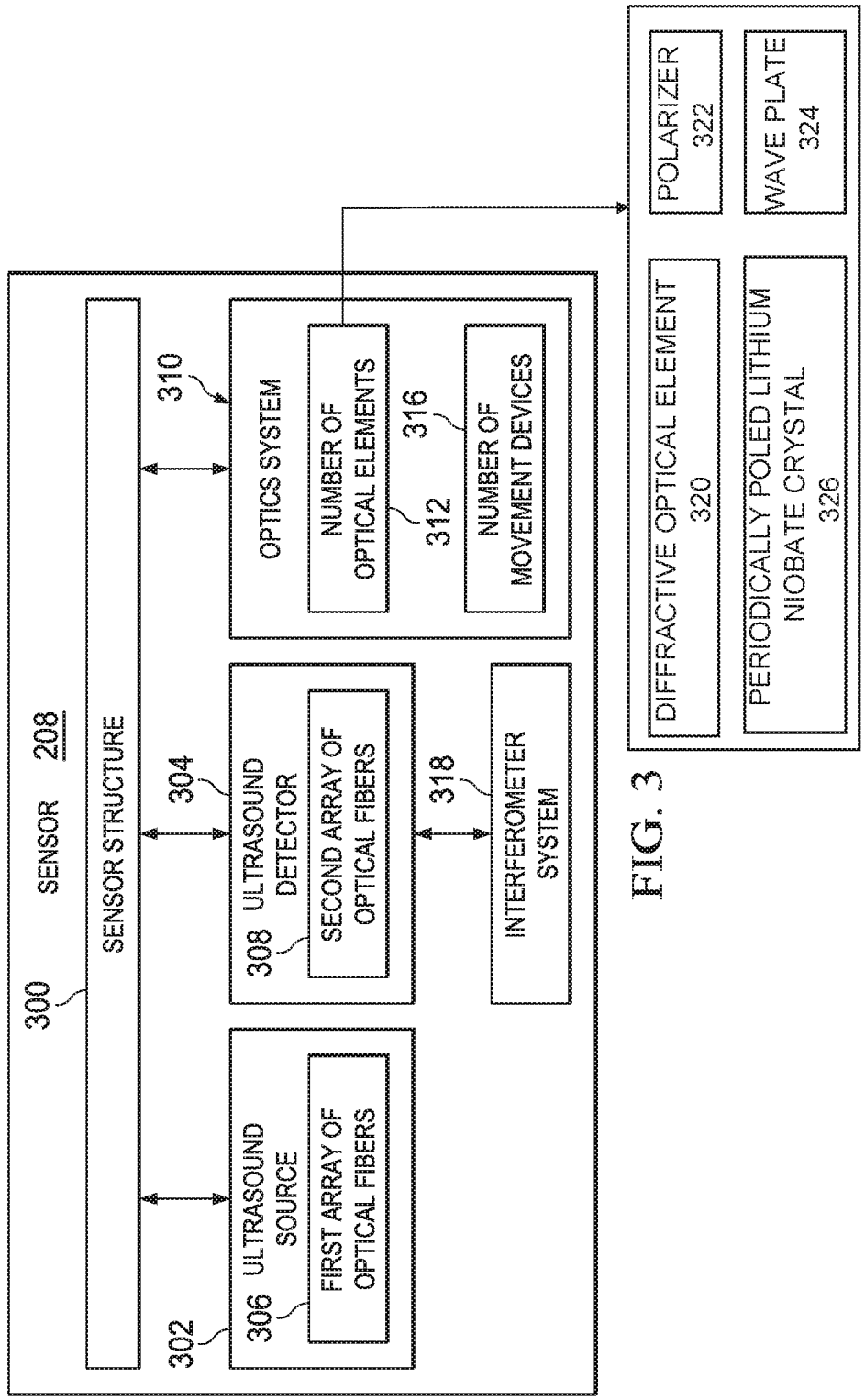
FIG. 3 is an illustration of a block diagram of a sensor in accordance with an illustrative embodiment.

With reference now to FIG. 3, an illustration of a block diagram of a sensor is depicted in accordance with an illustrative embodiment. Examples of components in sensor 208 are shown in this figure.

As depicted, sensor 208 includes sensor structure 300, ultrasound source 302, and ultrasound detector 304. Sensor structure 300 may take a number of different forms. For example, sensor structure 300 may be a housing, a frame, or some other suitable type of physical structure. In one illustrative example, sensor structure 300 may take the form of an end effector configured for attachment to a robot such as end effector 110 for robot 108 in FIG. 1.

In these illustrative examples, ultrasound source 302 and ultrasound detector 304 are associated with sensor structure 300. Ultrasound source 302 is configured to transmit first light 216, while ultrasound detector 304 is configured to detect sound waves 233 in first response 232 in response to sound waves 230.

When one component is "associated" with another component, the association is a physical association in these depicted examples. For example, a first component, ultrasound source 302, may be considered to be associated with a second component, sensor structure 300, by being secured to the second component, bonded to the second component, mounted to the second component, welded to the second component, fastened to the second component, and/or connected to the second component in some other suitable manner. The first component also may be connected to the second component using a third component. The first component may also be considered to be associated with the second component by being formed as part of and/or an extension of the second component.

Ultrasound source 302 is comprised of first array of optical fibers 306. First array of optical fibers 306 is configured to receive first light 216 from light source 210 and transmit first light 216 in the form of first pattern 222 onto surface 218 of test object 202. First light 216 from first array of optical fibers 306 is configured to cause excitation in test object 202. In other words, first light 216 from first array of optical fibers 306 is configured to generate sound waves 230 within test object 202.

As depicted, ultrasound detector 304 is comprised of second array of optical fibers 308. Second array of optical fibers 308 is configured to transmit second light 234 and detect second response 238 to second light 234. Second light 234 is not configured to generate sound waves 230 within test object 202. Instead, second light 234 is configured to reflect, scatter, or otherwise interact with surface 218 of test object 202, the air around surface 218 of test object 202, or both in a manner such that the portion of second light 234 that is received by second array of optical fibers 308 may be affected by sound waves 233 in first response 232 that reach surface 218 of test object 202.

In some illustrative examples, overlap is present in the time between the two patterns of light, first pattern 222 and second pattern 236, being transmitted onto surface 218. With this overlap, second array of optical fibers 308 may be used to monitor for first response 232 at the same time or prior to the generation of sound waves 230.

In other illustrative examples, each optical fiber in first array of optical fibers 306 may transmit first light 216 sequentially rather than at the same time. Additionally, groupings of optical fibers in first array of optical fibers 306 may sequentially transmit first light 216. Second light 234 may be transmitted in a similar fashion by second array of optical fibers 308. In still other illustrative examples, first light 216 may be transmitted using different phases, wavelengths, or both in addition to transmitting first light 216 through optical fibers in first array of optical fibers 306, second array of optical fibers 308, or both at different times.

Mechanisms such as delay lines and delay circuits separate lasers in light source 210. These mechanisms may reduce cross-talk in the optical fibers that results in first light 216 in first array of optical fibers 306 and second light 234 in second array of optical fibers 308 from exiting one optical fiber and entering another optical fiber. In other words, different phases, wavelengths, timings or some combination thereof may be used to reduce cross-talk between optical fibers within first array of optical fibers 306 and second array of optical fibers 308.

In these illustrative examples, sensor 208 also may include optics system 310. Optics system 310 is associated with sensor structure 300. As depicted, optics system 310 is a hardware system and may include components such as number of optical elements 312, number of movement devices 316, and other suitable components.

Optics system 310 is configured to direct the transmission of first light 216 and second light 234 to surface 218 of test object 202. Further, optics system 310 also may direct second response 238 to second array of optical fibers 308.

Number of optical elements 312 is configured to modify the transmission of first light 216 and second light 234 in these illustrative examples. Number of optical elements 312 may include at least one of a lens, a mirror, a diffractive optical element 320, a polarizer 322, a wave plate 324, a periodically-poled Lithium niobate crystal 326, or other suitable optical elements.

For example, number of optical elements 312 may be configured to shape first light 216 transmitted from first array of optical fibers 306 to form first pattern 222. In a similar fashion, number of optical elements 312 may be used to shape second light 234 transmitted from second array of optical fibers 308 to form areas 237 in second pattern 236 with a desired size. Number of optical elements 312 also may be used to change the polarization of first light 216 and second light 234, the color of first light 216 and second light 234, and other parameters of first light 216 and second light 234.

In these illustrative examples, number of movement devices 316 may be used to move one or more of number of optical elements 312 to cause movement of first pattern 222 of first light 216 and second pattern 236 of second light 234. This movement may occur without moving sensor structure 300 in this illustrative example. Number of movement devices 316 may include, for example, at least one of a motor, an actuator, and other suitable types of devices that may be configured to move number of optical elements 312.

Sensor 208 also may include interferometer system 318. Interferometer system 318 is a hardware device and is configured to identify information from the light forming second response 238. Interferometer system 318 may include one or more interferometers in these illustrative examples. The information identified by interferometer system 318 may include, for example, displacements, deflections, surface velocity, and other information that may be used to identify second response 238 as detected by second array of optical fibers 308 receiving the light in second response 238.

In some illustrative examples, interferometer system 318 may be considered part of ultrasound detector 304 even though interferometer system 318 may not be located in sensor structure 300. Interferometer system 318 may be associated with optics system 310 or may be in a separate location.

Figure 4:
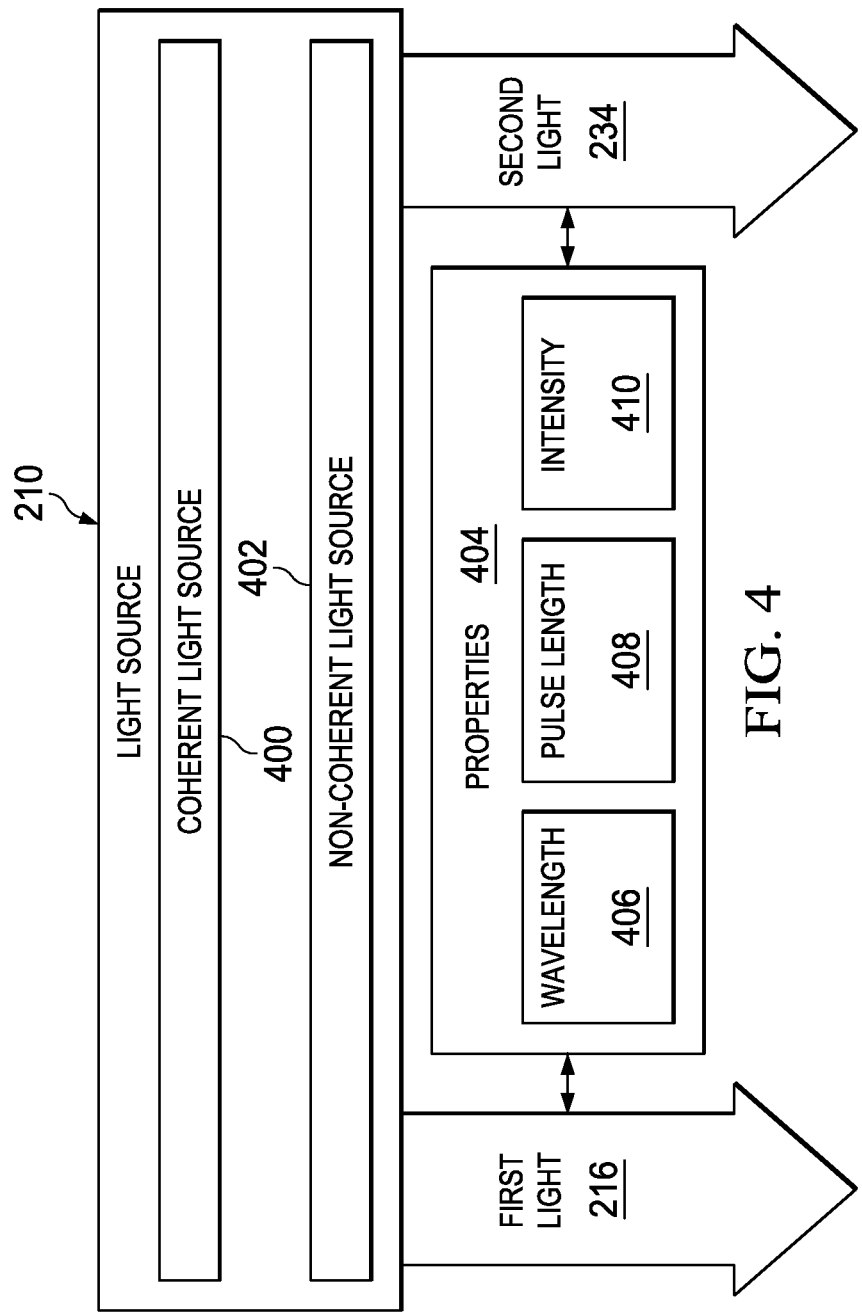
FIG. 4 is an illustration of a block diagram of a light source in accordance with an illustrative embodiment.

Turning now to FIG. 4, an illustration of a block diagram of a light source is depicted in accordance with an illustrative embodiment. In these illustrative examples, light source 210 may be, for example, at least one of coherent light source 400 and non-coherent light source 402. Coherent light source 400 may be, for example, a laser, an array of laser diodes, or some other suitable source of coherent light. Non-coherent light source 402 may be, for example, an array of light emitting diodes, xenon light, or some other suitable source of non-coherent light.

As depicted, light source 210 is configured to generate, first light 216, and second light 234 with properties 404. Properties 404 include wavelength 406, pulse length 408, and intensity 410. Properties 404 may be different for first light 216 and second light 234

Wavelength 406 may be selected based on the material forming test object 202, the thickness of test object 202, and other suitable factors. Wavelength 406 may be selected for first light 216 in a manner that increases absorption of energy from first light 216 when first light 216 and second light 234 are transmitted onto surface 218 of test object 202. For example, when test object 202 is comprised of one or more composite materials, wavelength 406 selected for first light 216 may be from about 300 millimeters to about 30,000 millimeters. Wavelength 406 may be the same for generating both sound waves 230 and first response 232.

Pulse length 408 may be selected for first light 216 to generate a desired frequency for sound waves 230. For example, a pulse duration of about 1 nanosecond to about 200 nanoseconds may be used. Pulse length 408 may be selected to have a duration of about 50 microseconds to about 100 microseconds for second light 234 that is used to detect sound waves 233 in first response 232.

Intensity 410 is selected based on the amount of energy that is desired to be transmitted into test object 202 by first light 216 encountering surface 218 of test object 202. Intensity 410 may be selected for first light 216 to provide a desired level of sound waves 230 when first light 216 is transmitted onto surface 218 of test object 202. Intensity 410 may be selected for first light 216 and second light 234 to reduce or avoid damage to surface 218 of test object 202. Of course, the intensity also may vary depending on the values selected for pulse length 408.

Although specific values have been specified for properties 404, these values are only presented for purposes of illustration and not meant to limit other values that may be used. The selection of properties 404 may vary depending on light source 210, materials in test object 202, and other factors.

The illustration of inspection environment 200 and the different components in inspection environment 200 in FIGS. 2-4 are not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, in some illustrative embodiments, ultrasound source 302 and ultrasound detector 304 may be placed in separate sensor structures. In other illustrative examples, sensor 208 may be moved by a human operator rather than a robot or other type of machine. In other words, movement system 206 may take the form of a human operator.

In still another illustrative example, optics system 310 may be implemented using more than one block. For example, optics system 310 may be part of ultrasound source 302, ultrasound detector 304, or both rather than being a separate block.

In another illustrative example, test object 202 may be an object for other types of platforms other than an aircraft. The platform in which the test object may be located may be, for example, a mobile platform, a stationary platform, a land-based structure, an aquatic-based structure, and a space-based structure. More specifically, the platform, may be a surface ship, a tank, a personnel carrier, a train, a spacecraft, a space station, a satellite, a submarine, an automobile, a power plant, a bridge, a dam, a manufacturing facility, a building, and other suitable platforms.

Figure 5:
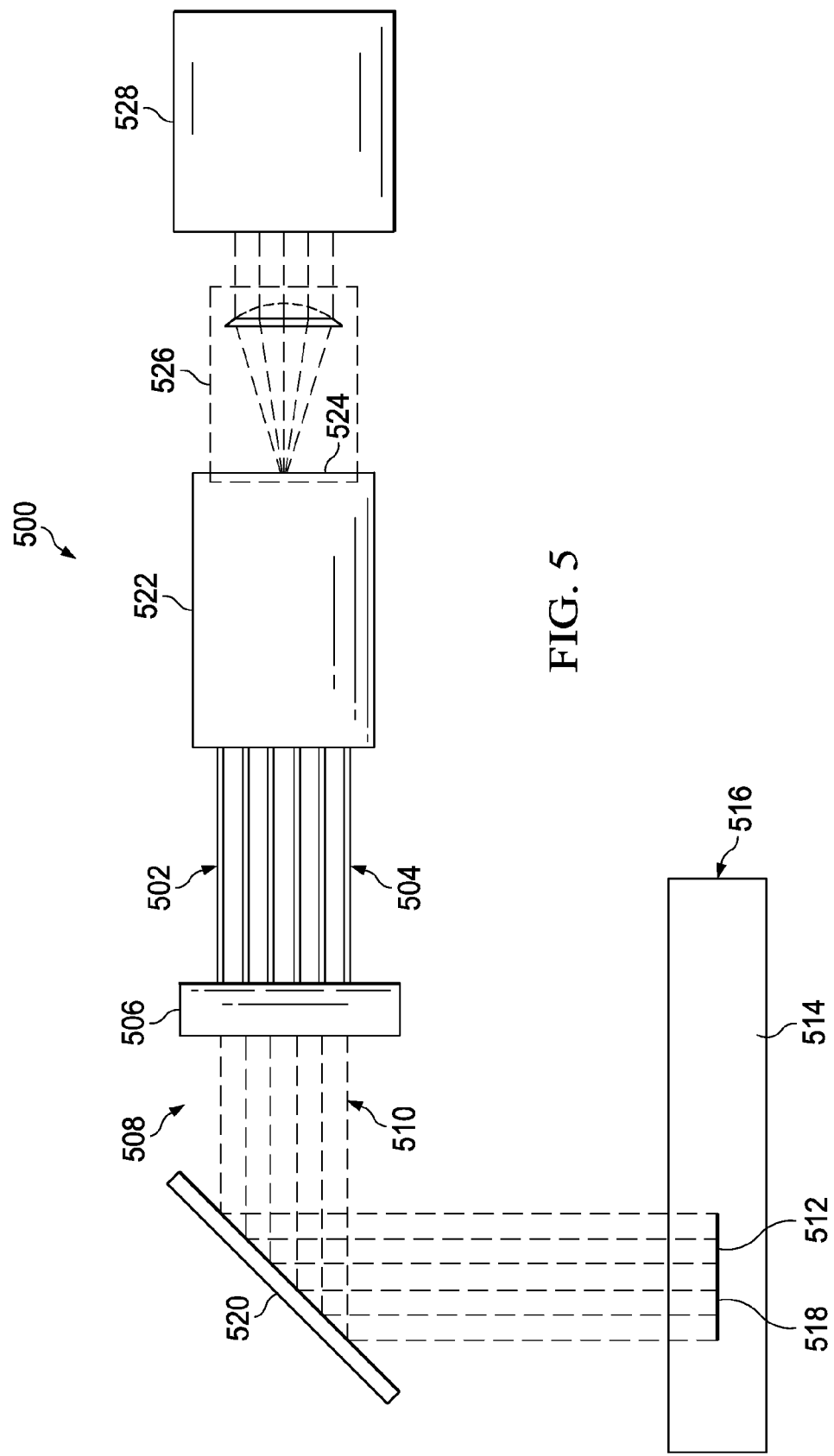
FIG. 5 is an illustration of an ultrasound source in accordance with an illustrative embodiment.

Turning now to FIG. 5, an illustration of an ultrasound source is depicted in accordance with an illustrative embodiment. Ultrasound source 500 is an example of one implementation for ultrasound source 302 shown in block form in FIG. 3.

In this illustrative example, optical fibers 502 are arranged in array 504. Optical fibers 502 may be implemented using any type of optical fiber that is configured to carry light within the optical fibers.

In this illustrative example, six optical fibers are present in optical fibers 502. Array 504 is a 1×6 array in this illustrative example. Of course, other numbers of optical fibers and other types of arrays may be used. For example, optical fibers 502 may include three fibers, fifteen fibers, twenty-seven fibers, or some other suitable number of fibers. Further, in some illustrative examples, the array may have two or more rows instead of a single row of optical fibers.

Ultrasound source 500 also includes cylinder lens 506. Cylinder lens 506 is configured to cause light 508 transmitted by array 504 of optical fibers 502 to form beams 510 which has a linear shape. Cylinder lens 506 is configured to shape light 508. In particular, cylinder lens 506 is configured to cause light 508 to form pattern 512 on surface 514 of test object 516 as a continuous line. In this illustrative example, cylinder lens 506 may function to cause pattern 512 of light 508 to have an intensity with a Gaussian profile. In this illustrative example, the Gaussian profile is in an X and Y direction relative to a plane on surface 514 of test object 516.

In these illustrative examples, if optical fibers 502 in array 504 are spaced far enough apart, then a pattern of individual areas is formed on surface 514 of test object 516. Each area is "approximately a Gaussian profile" in both X and Y directions. Cylinder lens 506 causes the Gaussian profiles to be different in the X and Y directions.

In particular, cylinder lens 506 is configured to reduce divergence in a manner such that beams 510 are focused in one direction and form pattern 512 when reaching surface 514 of test object 516. In these illustrative examples, pattern 512 takes the form of line 518. Line 518 may be formed from the intersection or overlapping of beams 510 on surface 514 of test object 516. Without cylinder lens 506, the divergence of beams 510 may be in two dimensions resulting in an oval or circular shape rather than a line.

In this example, mirror 520 is an example of a component that may be used to implement optics system 310 in FIG. 3. Mirror 520 is configured to manage the direction in which beams 510 of light 508 travel to reach surface 514 of test object 516.

As depicted, optical fibers 502 may be grouped and covered to form fiber bundle 522. In this illustrative example, end 524 of fiber bundle 522 is connected to collimator 526.

Collimator 526 is connected to laser 528. Laser 528 is the source of light 508. As depicted, light 508 is sent through collimator 526. Collimator 526 is configured to make light 508 coherent in these illustrative examples.

Figure 6:
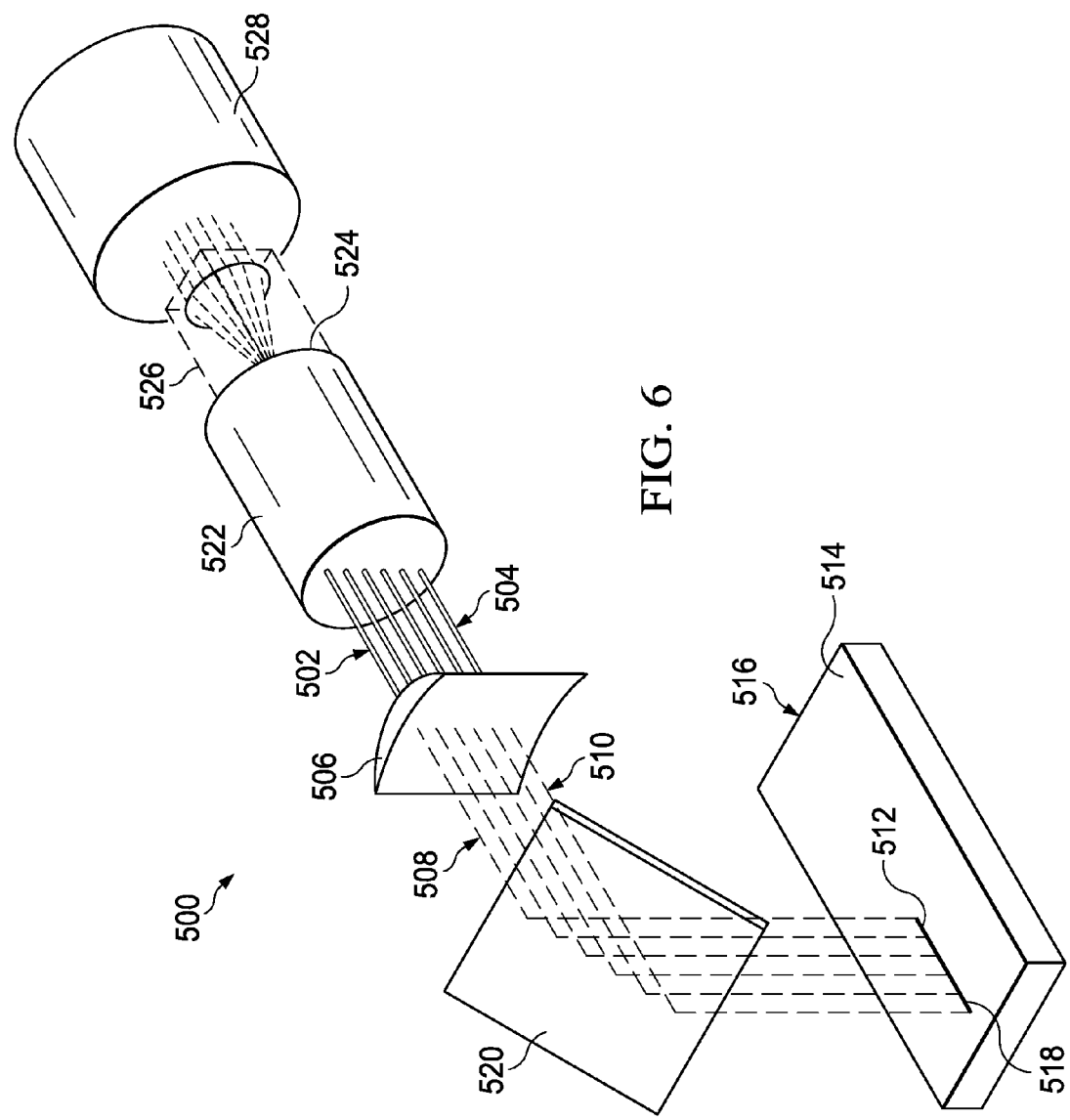
FIG. 6 is an illustration of an ultrasound source in accordance with an illustrative embodiment.

Turning now to FIG. 6, an illustration of an ultrasound source is depicted in accordance with an illustrative embodiment. In this depicted example, ultrasound source 500 is shown in a perspective view.

Figure 7:
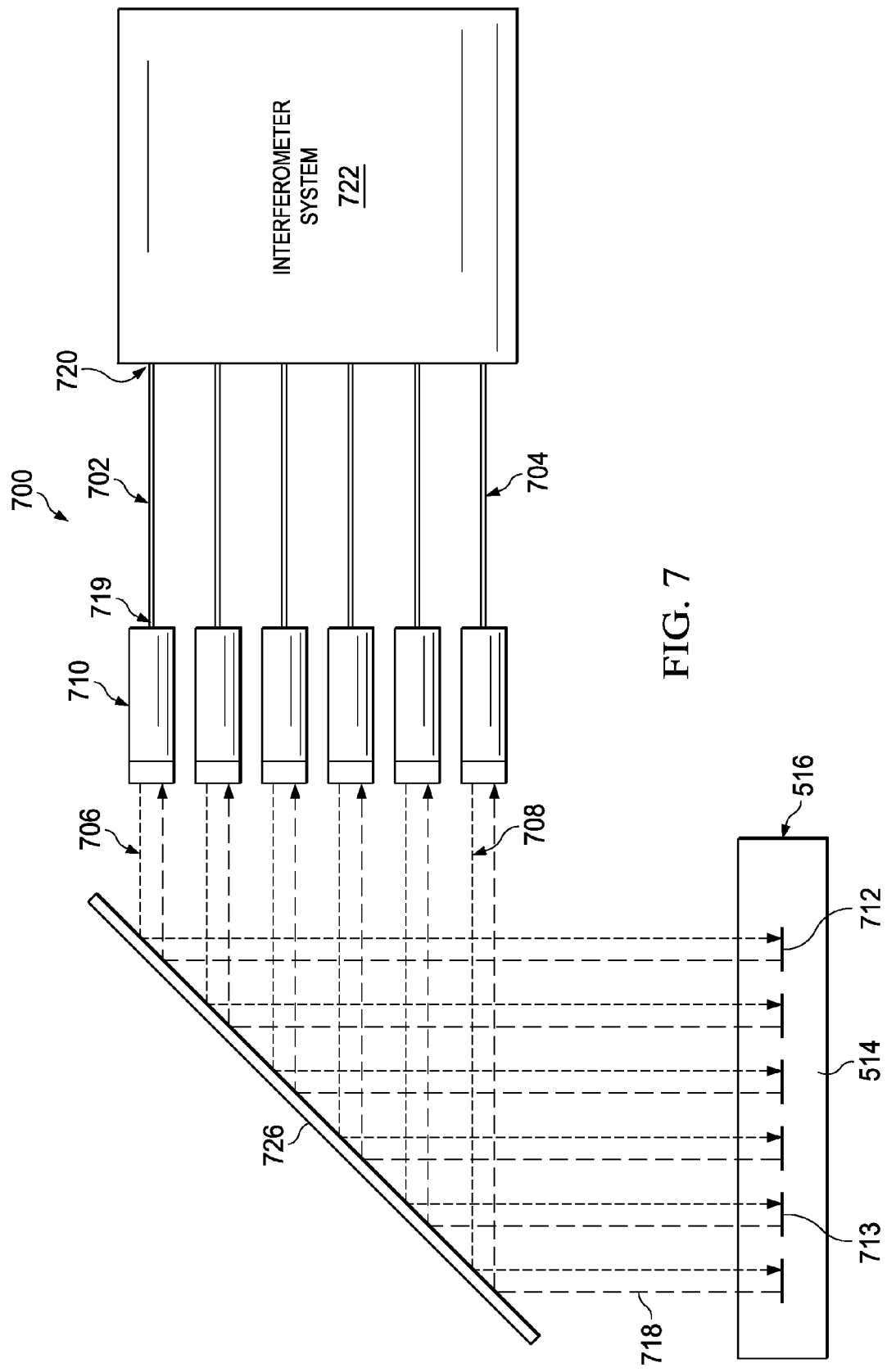
FIG. 7 is an illustration of an ultrasound detector in accordance with an illustrative embodiment.

Turning now to FIG. 7, an illustration of an ultrasound detector is depicted in accordance with an illustrative embodiment. Ultrasound detector 700 is an example of one implementation for ultrasound detector 304 shown in block form in FIG. 3. As depicted, ultrasound detector 700 includes optical fibers 702. Optical fibers 702 are arranged as array 704. Array 704 of optical fibers 702 is configured to emit beams 706 of light 708.

In this illustrative example, six optical fibers are present in optical fibers 702. Additionally, array 704 is a 1×6 array. Of course, other numbers of optical fibers and other configurations for array 704 may be present depending on the particular implementation.

In this illustrative example, ultrasound detector 700 also includes collimators 710. As depicted, each optical fiber in optical fibers 702 is associated with a collimator in collimators 710.

In these illustrative examples, collimators 710 may be implemented using different types of collimators. For example, without limitation, collimators 710 may be selected from at least one of an aspherical lens collimator, a spherical lens collimator, a grin lens collimator, or some other suitable type of collimator. Collimators 710 are used to change light 708 into coherent light in these illustrative examples.

Light 708 is comprised of light waves that are in phase with each other. With light 708, the phases of the electromagnetic waves at each point on a line normal to the direction of which beams 706 are traveling is identical.

In this illustrative example, beams 706 of light 708 form pattern 712 on surface 514 of test object 516. In this illustrative example, pattern 712 is in the form of line 713. Line 713 of pattern 712 is a non-continuous line in this illustrative example. In other illustrative examples, line 713 of pattern 712 may be a continuous line.

In this illustrative example, light 708 transmitted by optical fibers 702 onto surface 514 of test object 516 results in response 718. Response 718 is comprised of light. The light in response 718 is caused by interaction with surface 514. For example, light 708 may reflect, scatter, or reflect and scatter off of surface 514.

Response 718 is detected at end 719 of optical fibers 702 and may be transmitted through optical fibers 702 in a direction opposite to the transmission of light 708. In this illustrative example, end 720 of optical fibers 702 in array 704 are connected to interferometer system 722. Interferometer system 722 is the source of light 708 and receives response 718.

In this illustrative example, mirror 726 is an example of a component that may be used to implement optics system 310 in FIG. 3. Mirror 726 is configured to control the direction in which light 708 and response 718 travel.

Figure 8:
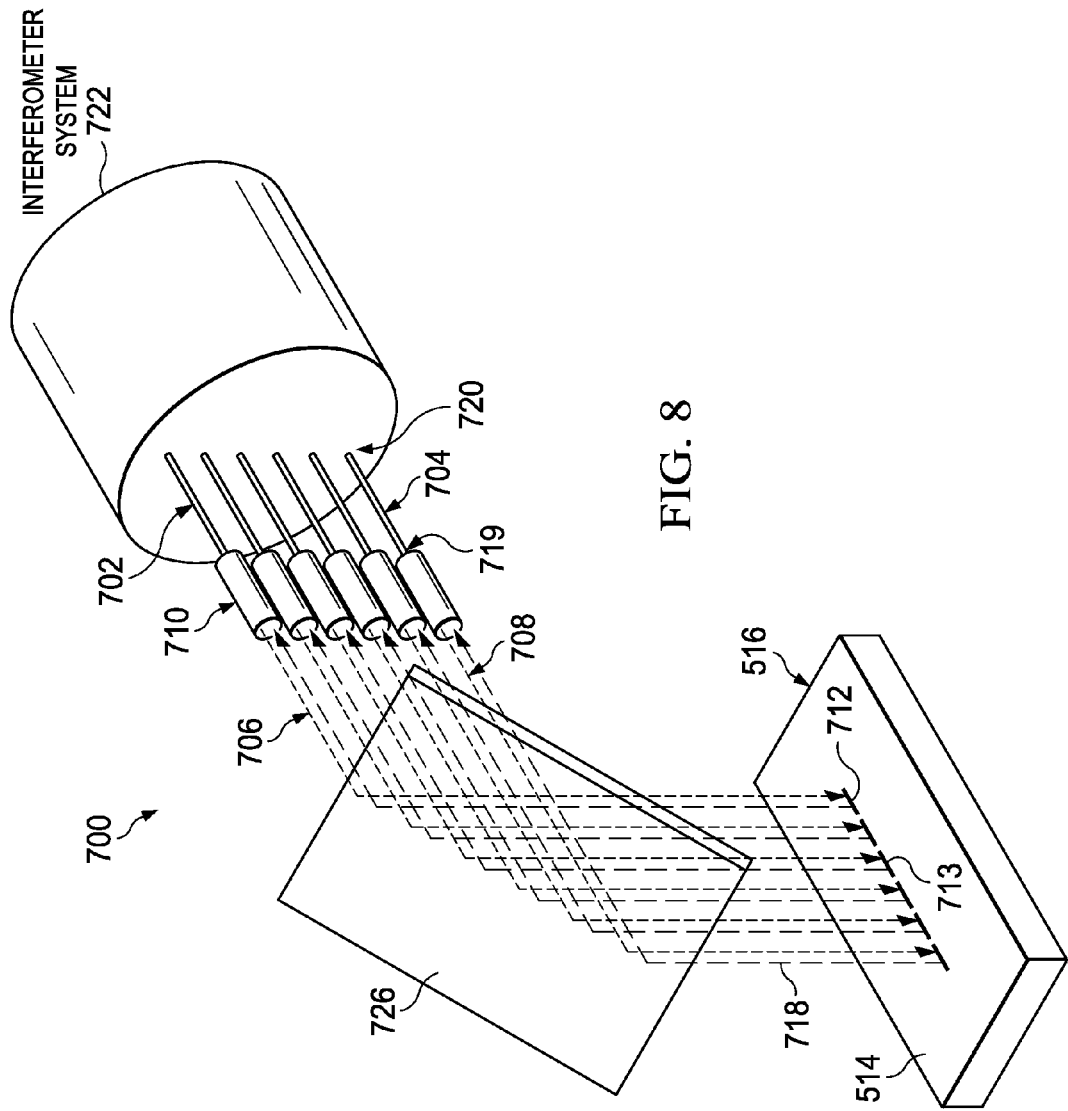
FIG. 8 is an illustration of an ultrasound detector in accordance with an illustrative embodiment.

Turning now to FIG. 8, an illustration of an ultrasound detector is depicted in accordance with an illustrative embodiment. In this illustrative example, a perspective view of ultrasound detector 700 is shown.

Figure 9:
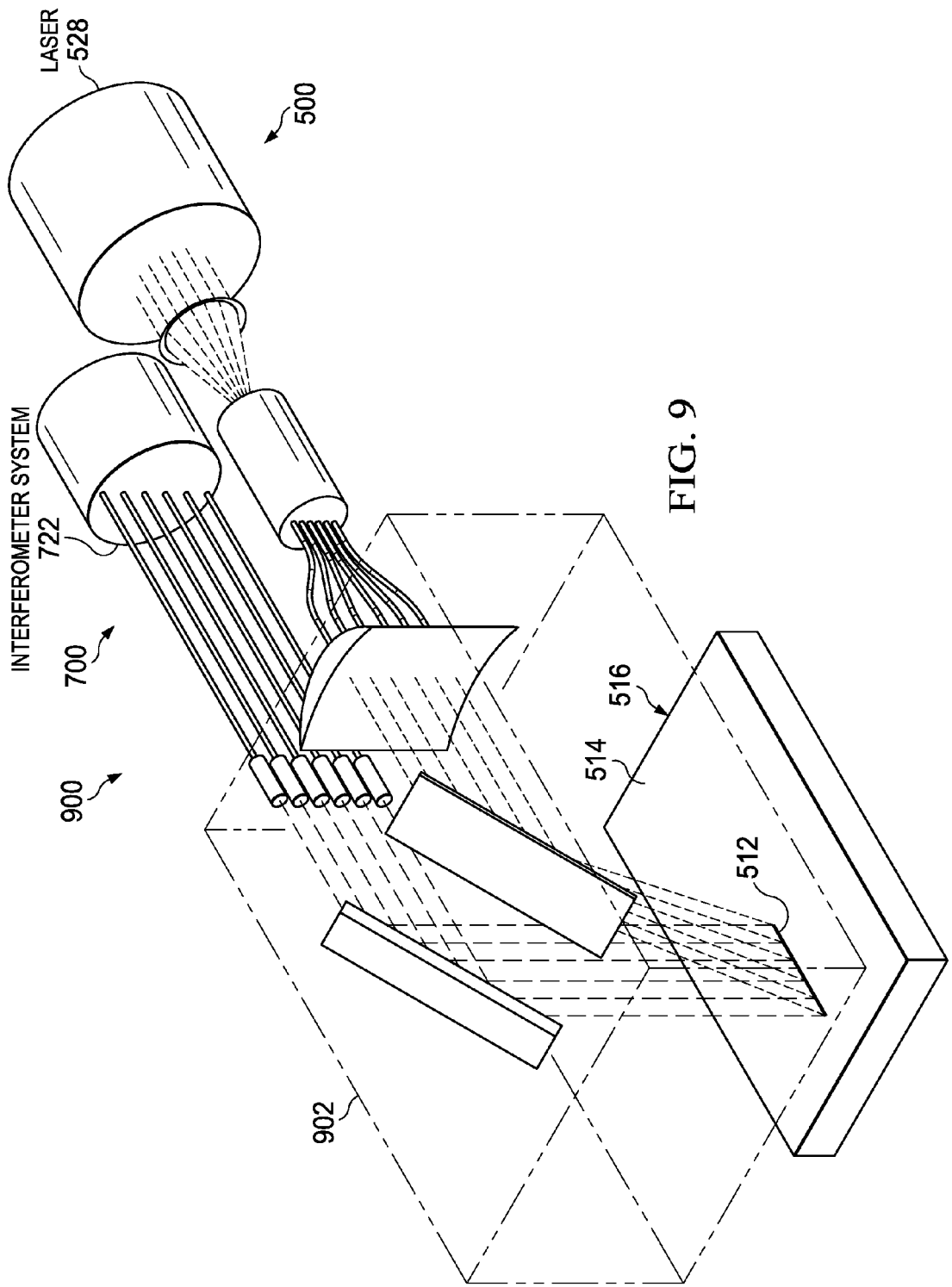
FIG. 9 is an illustration of an ultrasound inspection system in accordance with an illustrative embodiment.

Turning now to FIG. 9, an illustration of an ultrasound inspection system is depicted in accordance with an illustrative embodiment. In this depicted example, a perspective view of ultrasound inspection system 900 is shown. In this example, ultrasound inspection system 900 includes ultrasound source 500, ultrasound detector 700, and sensor structure 902.

Sensor structure 902 takes the form of a housing for an end effector in this illustrative example. As depicted, components for ultrasound source 500 and ultrasound detector 700 are located inside of sensor structure 902 but not seen in this example.

Figure 10:
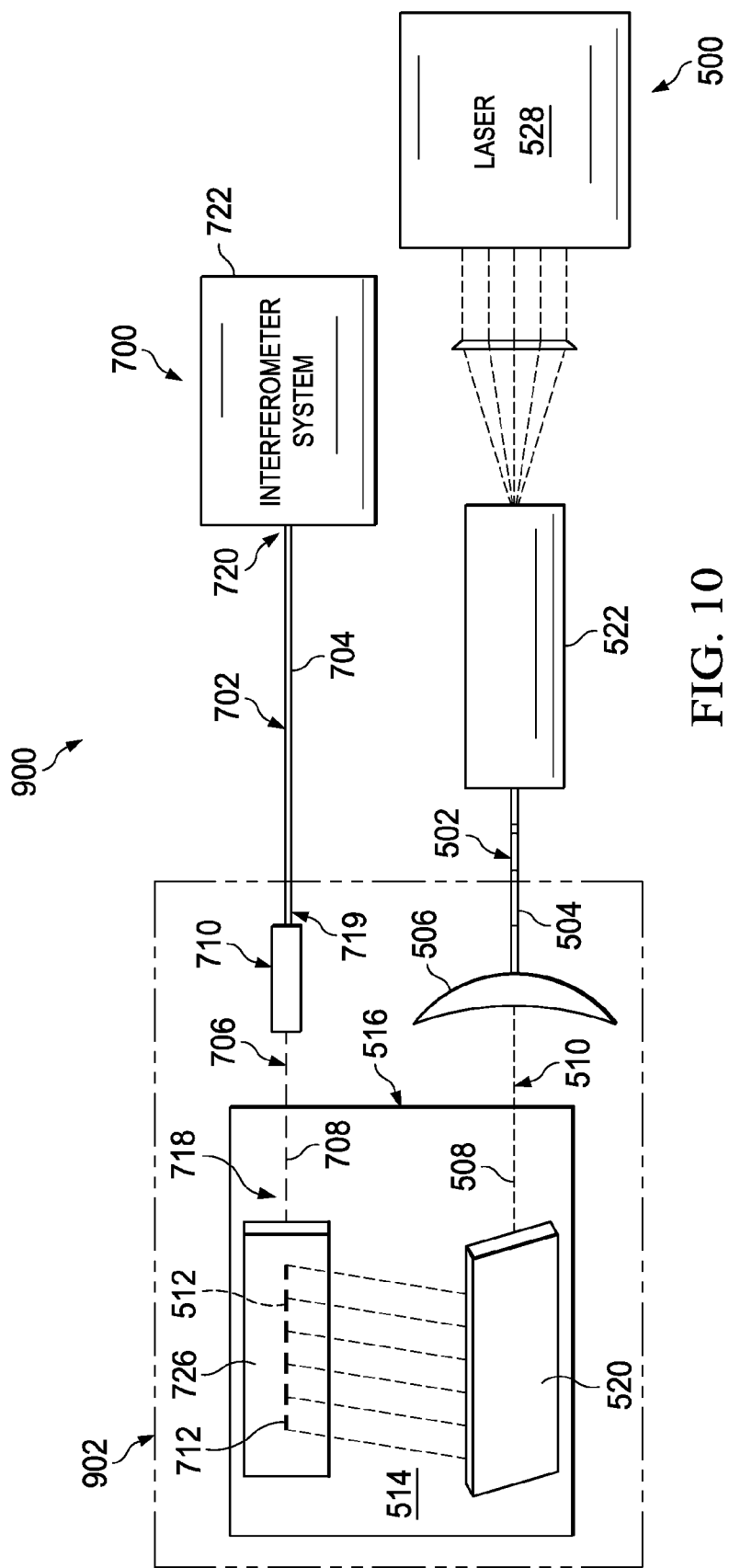
FIG. 10 is an illustration of a top view of an ultrasound inspection system in accordance with an illustrative embodiment.

Turning next to FIG. 10, an illustration of a top view of an ultrasound inspection system is depicted in accordance with an illustrative embodiment. In this view, sensor structure 902 may be positioned over surface 514 of test object 516 to perform inspection of test object 516.

In this illustrative example, pattern 512 and pattern 712 are aligned with each other on surface 514 of test object 516. In other words, pattern 512 is transmitted onto the same location as pattern 712 in this illustrative example. As a result, these two patterns substantially overlap each other.

Pattern 512 of light 508 is configured to generate sound waves within test object 516. Responses to sound waves may cause vibrations in surface 514 of test object 516. Pattern 712 of light 708 is configured to generate response 718 which includes variations or changes in surface 514 due to vibrations caused by the response to the sound waves. Response 718 is detected by optical fibers 702.

In these illustrative examples, laser 528 generates light 508. Light 508 is collimated by collimator 526 in this illustrative example. This collimated light is then transmitted through optical fibers 502 in the manner described with respect to FIG. 5 and FIG. 6.

In these illustrative examples, light 708 may be generated by interferometer system 722. Response 718 to light 708 may travel through optical fibers 702 back to interferometer system 722. Interferometer system 722 may use response 718 to generate data used to determine whether an inconsistency is present in test object 516.

Figure 11:
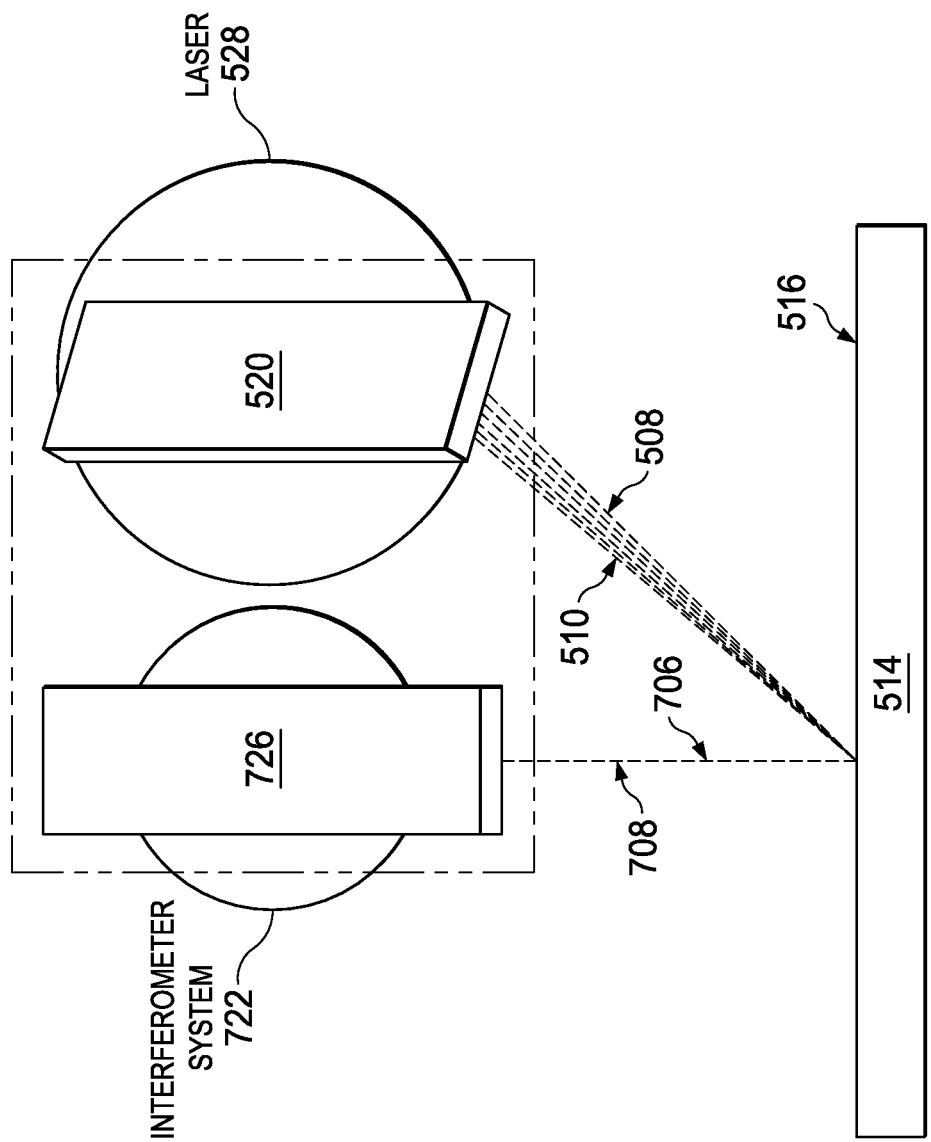
FIG. 11 is an illustration of a front view of an ultrasound inspection system in accordance with an illustrative embodiment.

Turning now to FIG. 11, an illustration of a front view of an ultrasound inspection system is depicted in accordance with an illustrative embodiment. In this illustrative example, another cross-sectional view of ultrasound inspection system 900 is shown.

Figure 12:
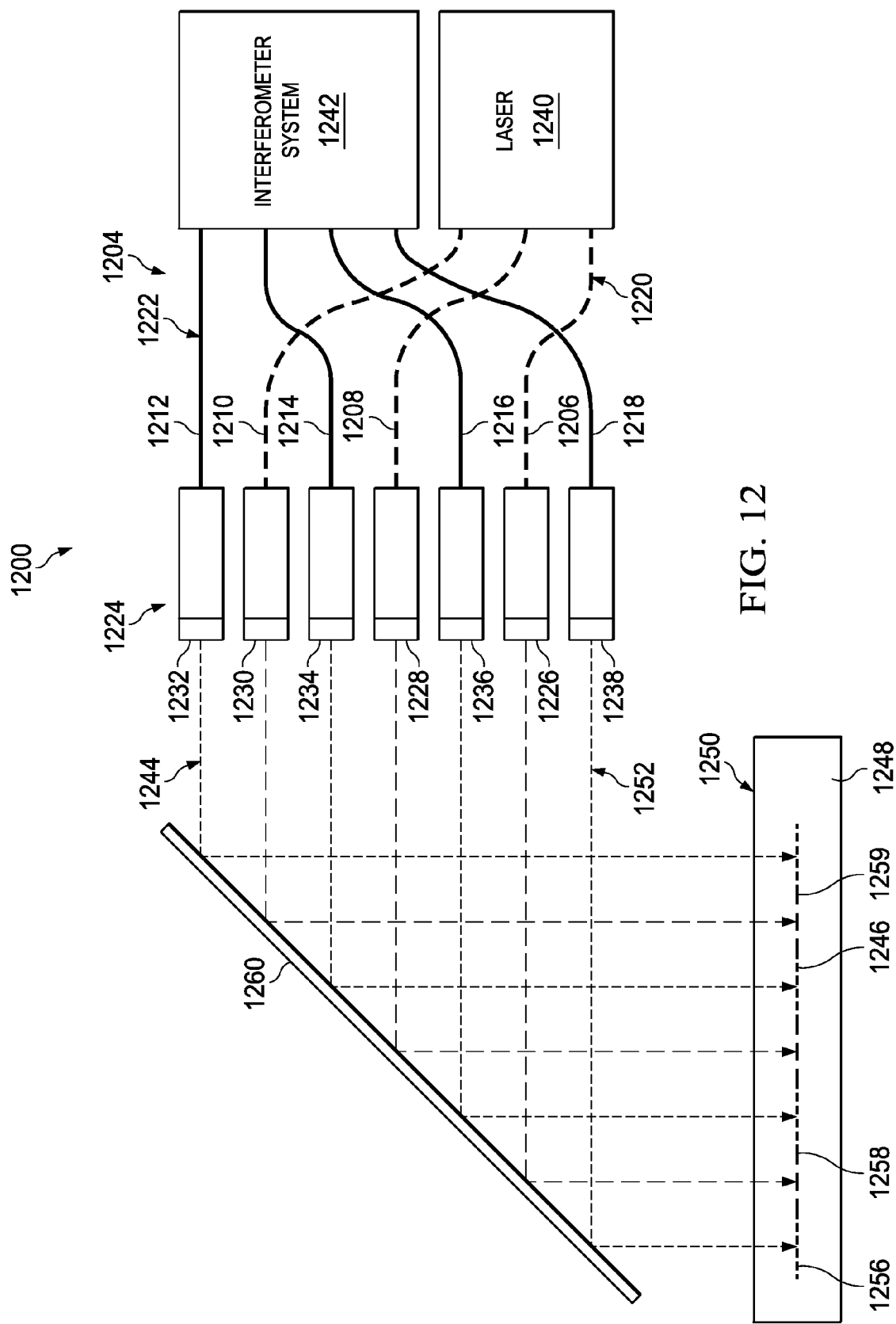
FIG. 12 is another illustration of an ultrasound inspection system in accordance with an illustrative embodiment.

Turning now to FIG. 12, another illustration of an ultrasound inspection system is depicted in accordance with an illustrative embodiment. As depicted, ultrasound inspection system 1200 is another example of an implementation for ultrasound inspection system 204 shown in block form in FIG. 2.

In this illustrative example, ultrasound inspection system 1200 includes optical fibers 1204. Optical fibers 1204 comprise optical fibers 1206, 1208, 1210, 1212, 1214, 1216, and 1218. Optical fibers 1206, 1208, and 1210 form first of optical fibers 1220. Optical fibers 1212, 1214, 1216, and 1218 form second array of optical fibers 1222.

In this illustrative example, optical fibers 1204 are associated with collimators 1224. Collimators 1224 comprise collimators 1226, 1228, 1230, 1232, 1234, 1236, and 1238. Collimators 1226, 1228, and 1230 are associated with optical fibers 1206, 1208, and 1210, respectively. Collimators 1232, 1234, 1236, and 1238 are associated with optical fibers 1212, 1214, 1216, and 1218, respectively. In this illustrative example, optical fibers 1206, 1208, and 1210, in first array of optical fibers 1220, are interspersed with optical fibers 1212, 1214, 1216, and 1218 in second array of optical fibers 1222.

In this illustrative example, first array of optical fibers 1220 is connected to laser 1240. Second array of optical fibers 1222 are connected to interferometer system 1242. In this illustrative example, light 1244 from first array of optical fibers 1220 is emitted in the form of pattern 1246 onto surface 1248 of test object 1250. Light 1252 from second array of optical fibers 1222 forms pattern 1256 on surface 1248 of test object 1250.

In this illustrative example, pattern 1246 of light 1244 and pattern 1256 of light 1252 are non-continuous lines. As depicted, pattern 1246 of light 1244 takes the form of line 1258, and pattern 1256 of light 1252 takes the form of line 1259. These two patterns of light encounter surface 1248 at substantially the same location. In other words, these two patterns of light would overlap each other if transmitted at the same time.

In this illustrative example, mirror 1260 is an example of an optical system that may be used to control the direction in which light 1244 and light 1252 travel. Mirror 1260 may be one implementation for optics system 310 shown in block form in FIG. 3.

Figure 13:
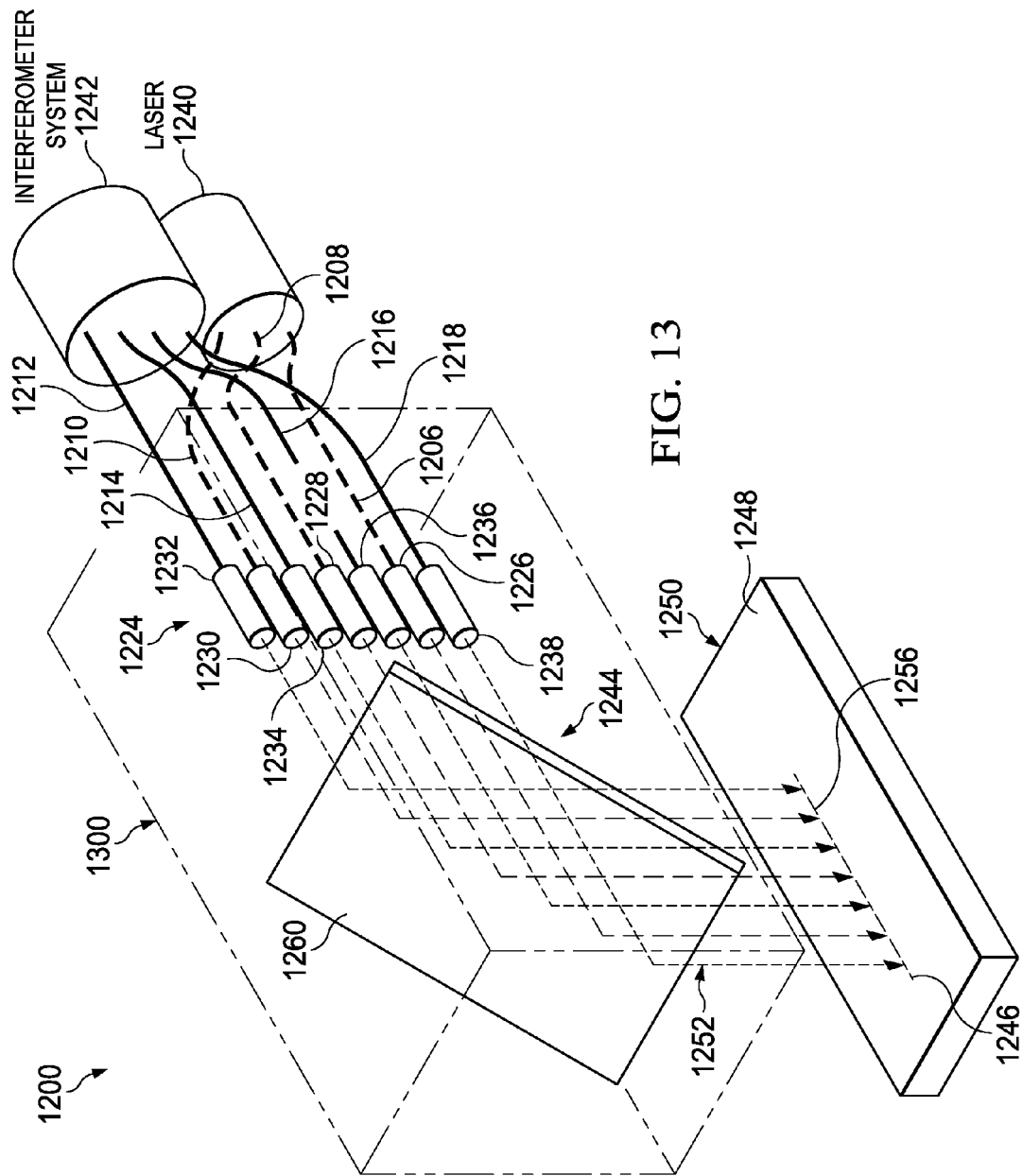
FIG. 13 is an illustration of a perspective view of an ultrasound inspection system in accordance with an illustrative embodiment.

Turning now to FIG. 13, an illustration of a perspective view of an ultrasound inspection system is depicted in accordance with an illustrative embodiment. In this perspective view, sensor structure 1300 is shown in phantom with some of the components in ultrasound inspection system 1200 located within sensor structure 1300.

The illustration of the different embodiments of an ultrasound inspection system in FIGS. 5-13 is not meant to imply limitations in the way in which other illustrative embodiments may be implemented. For example, other numbers of optical fibers may be used other than those depicted. In still other illustrative examples, the light source for the first array of optical fibers and the second array of optical fibers may be a single light source.

In yet another illustrative example, a diffractive diffuser may be used to shape light 508 emitted from array 504 of optical fibers 502. The diffractive diffuser may be used in addition to or in place of cylinder lens 506.

The different components shown in FIG. 1 and FIGS. 5-13 may be combined with components in FIGS. 2-4, used with components in FIGS. 2-4, or a combination of the two. Additionally, some of the components in FIG. 1 and FIGS. 5-13 may be illustrative examples of how components shown in block form in FIGS. 2-4 can be implemented as physical structures.

Figure 14:
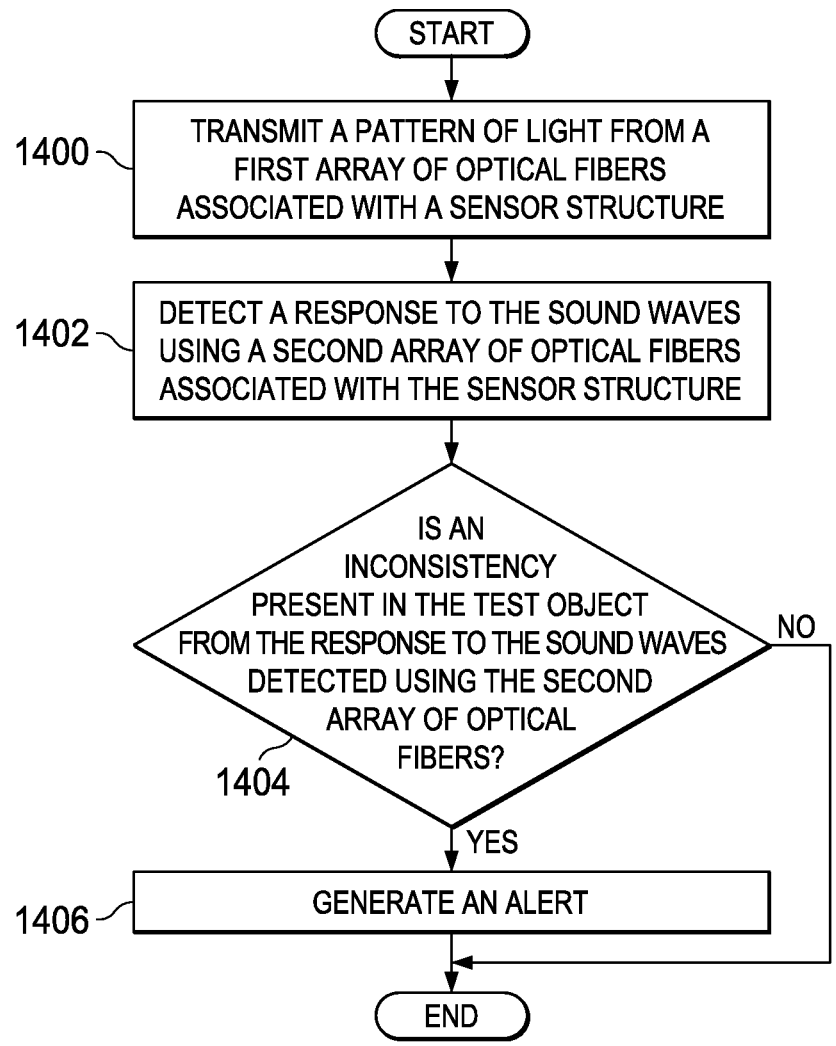
FIG. 14 is an illustration of a flowchart of a process for inspecting a test object in accordance with an illustrative embodiment.

Turning now to FIG. 14, an illustration of a flowchart of a process for inspecting a test object is depicted in accordance with an illustrative embodiment. The process illustrated in FIG. 14 may be implemented in an ultrasound inspection system such as ultrasound inspection system 204 in FIG. 2.

The process begins by transmitting a pattern of light from a first array of optical fibers associated with a sensor structure (operation 1400). The pattern of light is configured to cause sound waves in the test object when the pattern of light encounters the test object.

The process detects a response to the sound waves using a second array of optical fibers associated with the sensor structure (operation 1402). The second array of optical fibers transmits a second pattern of light in a manner that generates a response. This response is comprised of light that may have changes from the light in the response. The changes may be a result of changes in the surface caused by the response to the sound waves.

A determination is made as to whether an inconsistency is present in the test object from the response to the sound waves detected using the second array of optical fibers (operation 1404).

If an inconsistency is detected as being present in the test object, an alert is generated (operation 1406) with the process terminating thereafter. When an alert is generated, the test object may then be reworked or discarded. In some illustrative examples, operation 1406 may generate additional types of output in addition to the alert. For example, an image, a report, or both also may be generated in addition to the alert.

With reference again to operation 1404, if an inconsistency is not detected in the test object, the process also terminates. In this case, the test object has passed the inspection.

Figure 15:
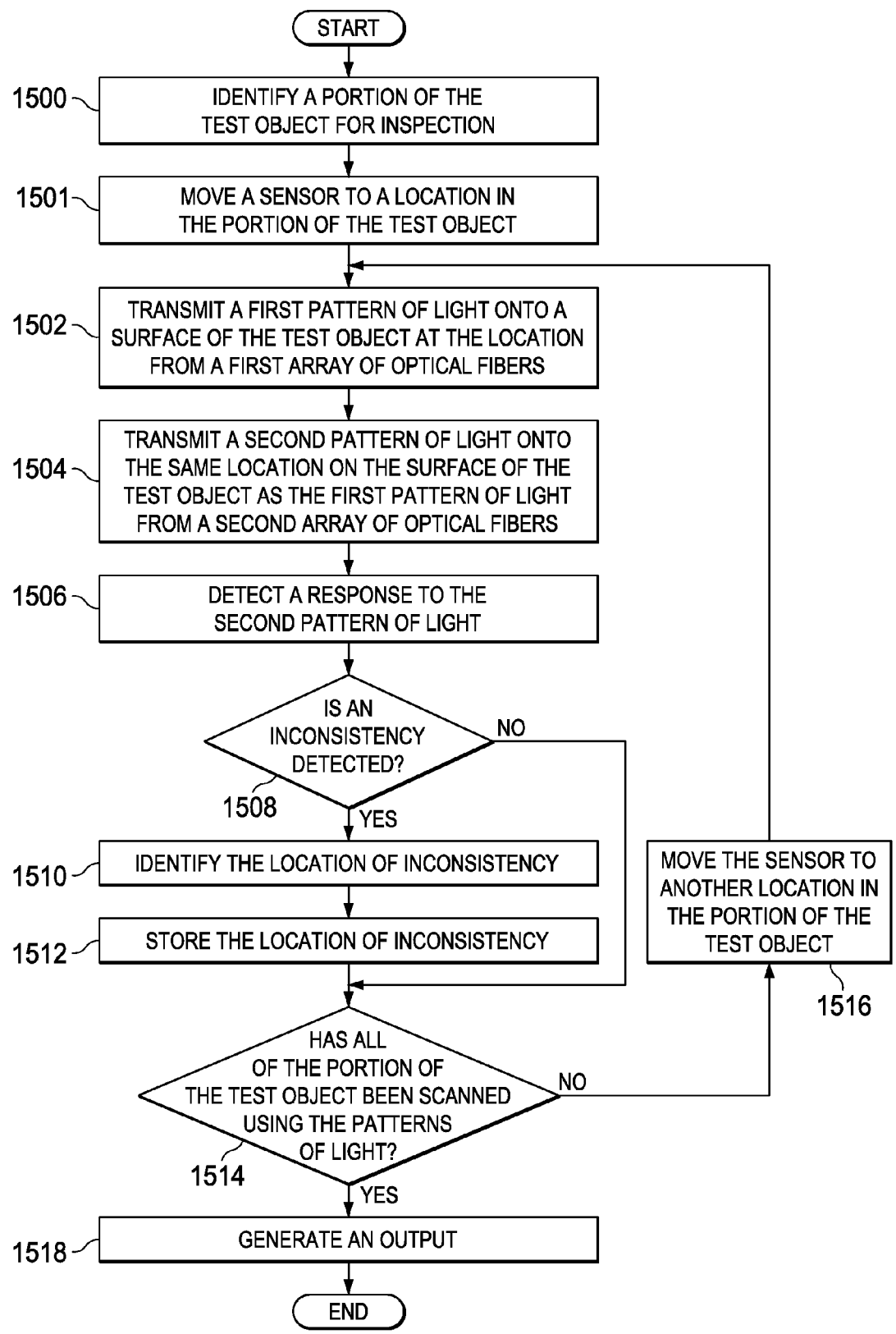
FIG. 15 is a flowchart of a process for scanning a test object in accordance with an illustrative embodiment.

Turning now to FIG. 15, a flowchart of a process for scanning a test object is depicted in accordance with an illustrative embodiment. In this illustrative example, the process in FIG. 15 may be implemented using ultrasound inspection system 204 in FIG. 2.

The process begins by identifying a portion of the test object for inspection (operation 1500). This portion of the test object may be some or the entire surface of the test object. For example, the portion of the test object may be a side, an edge, a radius, or some other portion of the test object.

A sensor is then moved to a location in the portion of the test object (operation 1501). In operation 1501, an orientation of the sensor may be adjusted to take into account a non-planar feature on the test object.

For example, the sensor may be positioned such that the pattern of light encompasses a non-planar feature not easily scanned by currently available laser ultrasound inspection systems. The non-planar feature may be, for example, a radius. The sensor may be moved in a linear direction along the length the radius.

In another illustrative example, the sensor may be positioned such that the pattern of light encompasses the margin of a part close to an edge where ultrasound coupling is difficult to achieve using currently available laser ultrasound inspection systems.

The process transmits a first pattern of light onto a surface of the test object at the location from a first array of optical fibers (operation 1502). In this illustrative example, the ray of light is transmitted in pulses and in a manner configured to cause sound waves in the test object. The location is a location in the portion of the test object that is to be inspected.

The process transmits a second pattern of light onto the same location on the surface of the test object as the first pattern of light from a second array of optical fibers (operation 1504). A response to the second pattern of light is detected (operation 1506). The response to the second pattern of light may be analyzed to identify a response to the sound waves that reach the surface of the test object.

A determination is made as to whether an inconsistency is detected (operation 1508). If an inconsistency is detected, the location of the inconsistency is identified (operation 1510). This location may be identified based on the response to sound waves detected using the response to the second pattern of light. The location of the inconsistency is stored (operation 1512).

A determination is made as to whether all of the portion of the test object has been scanned using the patterns of light (operation 1514). If all of the test object has not been scanned, the process moves the sensor to another location in the portion of the test object (operation 1516), with the process then returning to operation 1502 as described above.

If all of the portion of the test object has been scanned in operation 1514, an output is generated (operation 1518) with the process terminating thereafter. In operation 1518, the output may depend on whether one or more inconsistencies has been identified in the test object. If an inconsistency has been identified, at least one of an alert, an image with one or more graphical images identifying inconsistencies, a report, and other suitable types of output may be generated. Turning back to operation 1508, if an inconsistency is not detected, the process proceeds to operation 1514 as described above.

The different operations performed in FIG. 14 and FIG. 15 may be applied to test objects with planar and non-planar surfaces. These different operations may be performed for test objects that have non-planar features such as a radius, an edge, a groove, a ramp, a ply drop, a filler noodle, and other non-planar features.

Additionally, the different operations in FIG. 14 and FIG. 15 may be performed to inspect test objects more quickly than currently available laser ultrasound inspection systems that use a laser beam in the form of a point. Further, these operations may be performed without contact to the surface of a test object in contrast to laser ultrasound inspection systems that use piezoelectric transducers.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, segment, function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

For example, the operations in FIG. 15 may include an additional number of operations that cause the first pattern of light and the second pattern of light to move across a portion of the test object. These operations may be implemented in operation 1502, operation 1504, or both operations. In other words, the pattern of light transmitted in these operations may include transmitting them such that the pattern is moved over the location by moving one or more mirrors to different positions with a movement device.

This type of scanning may reduce the amount of physical movement of the sensor itself. Also, the speed at which the inspection of the test object is performed may be increased.

Illustrative embodiments of the disclosure may be described in the context of aircraft manufacturing and service method 1600 as shown in FIG. 16 and aircraft 1700 as shown in FIG. 17. Turning first to FIG. 16, an illustration of an aircraft manufacturing and service method is depicted in accordance with an illustrative embodiment. During pre-production, aircraft manufacturing and service method 1600 may include specification and design 1602 of aircraft 1700 in FIG. 17 and material procurement 1604.

During production, component and subassembly manufacturing 1606 and system integration 1608 of aircraft 1700 in FIG. 17 takes place. Thereafter, aircraft 1700 in FIG. 17 may go through certification and delivery 1610 in order to be placed in service 1612. While in service 1612 by a customer, aircraft 1700 in FIG. 17 is scheduled for routine maintenance and service 1614, which may include modification, reconfiguration, refurbishment, and other maintenance or service.

Each of the processes of aircraft manufacturing and service method 1600 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 17, an illustration of an aircraft is depicted in which an illustrative embodiment may be implemented. In this example, aircraft 1700 is produced by aircraft manufacturing and service method 1600 in FIG. 16 and may include airframe 1702 with plurality of systems 1704 and interior 1706. Examples of systems 1704 include one or more of propulsion system 1708, electrical system 1710, hydraulic system 1712, and environmental system 1714. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 1600 in FIG. 16.

One or more illustrative embodiments may be used during component and subassembly manufacturing 1606. For example, ultrasound inspection system 204 in FIG. 2 may be used to test different components generated during component and subassembly manufacturing 1606. In particular, ultrasound inspection system 204 may be used to test composite objects that form different parts for aircraft 1700. Further, ultrasound inspection system 204 also may be used to perform inspections during maintenance and service 1614. For example, aircraft 1700 may be inspected during scheduled maintenance for aircraft 1700. Further, ultrasound inspection system 204 also may be used to inspect composite parts used during maintenance and service 1614.

Thus, one or more illustrative embodiments may provide a method and apparatus for inspecting objects. In particular, the illustrative embodiments may be used to inspect objects such as composite parts without the need for physical contact with the part. Further, coupling mediums such as liquids, oils, and other types of coupling media may be unnecessary.

When using an ultrasound inspection system in accordance with an illustrative embodiment, light is used to generate sound waves and detect a response to the sound waves in the test object. With the illustrative embodiments, the movement of the laser beam may only need to be performed in one direction rather than two directions. The illustrative embodiments use a pattern of light rather than a point of light that is scanned across a surface in these illustrative examples.

Further, with the use of optical fibers, the end effector in which the optical fibers are located may be brought closer to the surface of the test object. Further, reduction in power of the laser sources may be achieved. As a result, ultrasound inspection system 204 may be performed without needing an eye-safe room or other safety measures typically associated with higher powered lasers.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for inspecting a test object with a non-planar feature using a platform, an interferometer system connected to the platform, an optical fiber carrier connected to and extending from the interferometer system, a fiber bundle inside the optical fiber carrier, the fiber bundle comprising a first plurality of optical fibers, the fiber bundle configured to receive and then transmit the light from a light source, an end effector disposed on an end of the optical fiber carrier, the end opposite the interferometer system, the light source in optical communication with the optical fiber carrier, the light source configured to emit a light, and a movement system connected to the optical fiber carrier, the method comprising:

moving, using the movement system, the optical fiber carrier over the non-planar feature of the test object;

causing, using a cylinder lens in optical communication with the first plurality of optical fibers, the light to have a first Gaussian profile in an "X" direction relative to a plane and a second Gaussian profile in a "Y" direction relative to the plane;

causing, using the cylinder lens, the first Gaussian profile and the second Gaussian profile to be different;

transmitting, using a first mirror in optical communication with the cylinder lens, light emitted from the cylinder lens in a pattern onto the non-planar feature of the test object, wherein the pattern is configured to cause sound waves in the test object and a response light from the test object;

receiving, at a second mirror, the response light;

receiving, at a plurality of collimators, the response light from the second mirror, wherein a second plurality of optical fibers is inside the optical fiber carrier, the second plurality of optical fibers connected to the plurality of collimators, each optical fiber of the second plurality of optical fibers connected to a corresponding collimator of the plurality of collimators;

receiving, at the interferometer system, the response light;

generating data from the response light; and determining, using the data, whether an inconsistency is present in the test object at the location of the non-planar feature.

2. The method of claim 1, wherein the platform comprises a robotic arm and the method further comprises:

moving the robotic arm over the non-planar surface.

3. The method of claim 1 further comprising:

generating an image of the test object with a graphical indicator for the inconsistency.

4. The method of claim 1 further comprising:
generating an alert if the inconsistency is present in the test object.

5. The method of claim 1, wherein the light source comprises a plurality of lasers, the method further comprising:
reducing cross-talk in optical fibers in the optical fiber carrier using a delay line and a delay circuit separating the plurality of lasers.

6. The method of claim 1, further comprising modifying transmission of the light using a number of optical elements.

7. The method of claim 1, wherein the light source is selected from the group consisting of: a laser and a xenon light.

8. The method of claim 1, wherein the non-planar feature is selected from one of an edge and a radius.

9. The method of claim 1, wherein the test object is comprised of a number of materials selected from one of a composite material, a plastic, and a metal.

10. The method of claim 1, wherein the test object is a composite part for an aircraft.

11. An apparatus comprising:
an interferometer system;
an optical fiber carrier connected to and extending from the interferometer system;
a light source in optical communication with the optical fiber carrier, the light source configured to emit a light;
a fiber bundle inside the optical fiber carrier, the fiber bundle comprising a first plurality of optical fibers, the fiber bundle configured to receive and then transmit the light from the light source;
a sensor structure connected to an end of the optical fiber carrier, the end opposite the interferometer system, the sensor structure comprising:
a cylinder lens in optical communication with the first plurality of optical fibers, wherein the cylinder lens is configured to cause the light to have a first Gaussian profile in an "X" direction relative to a plane and a second Gaussian profile in a "Y" direction relative to the plane, and wherein the cylinder lens is configured to cause the first Gaussian profile and the second Gaussian profile to be different;
a first mirror in optical communication with the cylinder lens, the first mirror further disposed such that light emitted from the cylinder lens is transmitted in a pattern of light onto a test object, wherein the pattern of light is configured to cause sound waves in the test object and a response light from the test object;
a second mirror and configured to receive the response light; and
a plurality of collimators configured to receive the response light from the second mirror;
a second plurality of optical fibers inside the optical fiber carrier, the second plurality of optical fibers connected to the plurality of collimators, each optical fiber of the second plurality of optical fibers connected to a corresponding collimator of the plurality of collimators; and
wherein the interferometer system is configured to receive the response light and generate data from the response light, the data used to determine whether an inconsistency is present in the test object at the location.

12. The apparatus of claim 11 further comprising a platform connected to the interferometer system, the platform comprising a robotic arm.

13. The apparatus of claim 11, wherein the optical fiber carrier comprises a hand-held tool.

14. The apparatus of claim 11 further comprising a movement system connected to the sensor structure, the movement system comprising a plurality of joints.

15. The apparatus of claim 11, wherein the light source comprises a plurality of lasers, the apparatus further comprising:
a delay line and a delay circuit separating the plurality of lasers, the delay line and the delay circuit configured to reduce cross-talk in optical fibers in the optical fiber carrier.

16. The apparatus of claim 11 further comprising:
a number of optical elements configured to modify transmission of the light.

17. The apparatus of claim 16, wherein the number of optical elements is selected from the group consisting of: a lens, a mirror, a diffractive optical element, a polarizer, a wave plate, and a periodically poled Lithium niobate crystal.

18. The apparatus of claim 11 further comprising:
a movement system connected to the optical fiber carrier, the movement system configured to move the optical fiber carrier into an opening of a test object, to move into a cavity of the test object, and to bypass a number of obstructions while moving the optical fiber carrier to a location that is inside the test object and obstructed from the opening by the number of obstructions while the interferometer system remains outside the opening.

* * * * *